(12) United States Patent
Robison

(10) Patent No.: US 6,309,849 B1
(45) Date of Patent: Oct. 30, 2001

(54) NUCLEIC ACID MOLECULES ENCODING HUMAN KINASE AND PHOSPHATASE HOMOLOGUES AND USES THEREFOR

(75) Inventor: Keith E. Robison, Wilmington, MA (US)

(73) Assignee: Millennium Pharamaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/387,212

(22) Filed: Aug. 31, 1999

(51) Int. Cl.[7] .............................. C12Q 1/48; C12N 9/12; C12N 15/00; C12N 5/00; C12N 1/20
(52) U.S. Cl. .................. 435/15; 435/194; 435/320.1; 435/325; 435/252.3
(58) Field of Search .................. 435/15, 194, 320.1, 435/325, 252.3

(56) References Cited
PUBLICATIONS

Hillier et al., EST Dtabase, Accession No. AA436054, 11/97.*

* cited by examiner

Primary Examiner—Rebecca E. Prouty
Assistant Examiner—M. Monshipouri
(74) Attorney, Agent, or Firm—Amy E. Mandragouras; Maria C. Laccotripe; Lahive & Cockfield, LLP

(57) ABSTRACT

The invention provides isolated nucleic acids molecules, designated Kinase and Phosphatase nucleic acid molecules, which encode novel protein kinase and protein phosphatase polypeptides. The invention also provides antisense nucleic acid molecules, recombinant expression vectors containing Kinase and Phosphatase nucleic acid molecules, host cells into which the expression vectors have been introduced, and nonhuman transgenic animals in which a Kinase and Phosphatase gene has been introduced or disrupted. The invention still further provides isolated Kinase and Phosphatase proteins, fusion proteins, antigenic peptides and anti-Kinase and Phosphatase antibodies. Diagnostic, screening, and therapeutic methods utilizing compositions of the invention are also provided.

5 Claims, 8 Drawing Sheets mine14803human_cl
GCAATTGATCCAATATCTGCAGGTTTCTAACACGCAAGCCAGGACAAAATACTCTTCAAG
GACGTGAACAGGAAGCTGAGTGATGTCTGGAAGGAGCTCTCGCTGTTACTTCAGGTTGAG
CAACGCATGCCTGTTTCACCCATAAGCCAAGGAGCGTCCTGGGCACAGGAAGATCAGCAG
GATGCAGACGAAGACAGGCGAGCTTTCCAGATGCTAAGAAGAGATAATGAAAAAATAGAA
GCTTCACTGAGACGATTAGAAATCAACATGAAAGAAATCAAGGAAACTTTGAGGCAGTAT
TTACCACCAAAATGCATGCAGGAGATCCGCAAGAGCAAATCAAGGAGATCAAGAAGGAG
CAGCTTTCAGGATCCCCGTGGATTCTGCTAAGGGAAAATGAAGTCAGCACACTTTATAAA
GGAGAATACCACAGAGCTCCAGTGGCCATAAAAGTATTCAAAAAACTCCAGGCTGGCAGC
ATTGCAATAGTGAGGCAGACTTTCAATAAGGAGATCAAAACCATGAAGAAATTCGAATCT
CCCAACATCCTGCGTATATTTGGGATTTGCATTGATGAAACAGTGACTCCGCCTCAATTC
TCCATTGTCATGGAGTACTGTGAACTCGGGACCCTGAGGGAGCTGTTGGATAGGGAAAAA
GACCTCACACTTGGCAAGCGCATGGTCCTAGTCCTGGGGGCAGCCCGAGGCCTATACCGG
CTACACCATTCAGAAGCACCTGAACTCCACGGAAAAATCAGAAGCTCAAACTTCCTGGTA
ACTCAAGGCTACCAAGTGAAGCTTGCAGGATTTGAGTTGAGGAAAACACAGACTTCCATG
AGTTTGGGAACTACGAGAGAAAAGACACGACAAGAGTCAAATCTACAGCATATCTCTCAC
CTCAGGAACTGGAAGATGTATTTTATCAATATGATGTAAAGTCTGAAATATACAGCTTTG
GAATCGTCCTCTGGGAAATCGCCACTGGAGATATCCCGTTTCAAGGCTGTAATTCTGAGA
AGATCCGCAAGCTGGTGGCTGTGAAGCGGCAGCAGGAGCCACTGGGTGAAGACTGCCCTT
CAGAGCTGCGGGAGATCATTGATGAGTGCCCGGGCCCATGATCCCTCTGTTGCGGCCCTC
TGTGGATGAAATCTTAAAGAAACTCTCCCACCTTTTCTAAGTAGTGTATCAAAATCTAAA
CCAAGGAGTCTCTGGACAAGAAGCTGGGAGAGGCACAAACTGGACATCATCTCCTCTTCT
CATATCCTTCGGCATTGGGTTATCTATGGGAGCAAGGAGTGGGCACGCTTCTCTGTTACA
AATAGAAAACGATTCCAGTCATACAGGACACATCCCACTCCAAATGATATTTCCAAAAAC
ATACCTCTGACAGTAACTTTGATAGATGGTTTGTCAAATGTATCTTTCTGGGTATCCACA
CCTCTTGGCAATGAAATTTGCAGCTCCTCCCTTCCATAAATGAAGTCTCTTTCCCCACCA
TTTGAATCTGGGCTGGCACTGTGACTTGATTTGATCAATAGAATGTGGAAGAAGTGACTG
TATGCCAGTTCCAAGCCTAGGTTTCAAGAGGCCTTATAAATGTCTGTTGGAACCTTACCC
AGCCATGAACATGTTGAGTGAGCATGCTGGAGAATGAGAGACCACATGAAGCAGAAACAT
GCTTTCCTAGCTGAAGTCATACTAGCCCAACCAACATGGCAGCTAACACATGAATGAGGC
CAATCAAGACCAGAAGAACCACTCAAGCAGATCCCAGCCCAAATTGCCCATTCACACAAT
CAGGAGCTAAATAAATTACTGTTGTCTTAAAAAAAAAAAAAAAANNNANANNANNNNAAN
AANNAAGG

Fig. 1 mine16328human_s1
TACTAAAGGGAATAAGCTTGCGGCCGCAATCTTTTTTTTTTTTTTTTTTTTTTTTTT
TTTTTCCTAAAANAAACCATTTATTGAAAAAAGAACCTTTTTCTTAAATTTCAGTAATCA
GCCTTTTGCATTACAAACCTGCAGCTTGCCAACAACAACAAAAAAGGTAANGGTTTCACA
AGTCAGNGCACTCAACAAACAGGAGATTAAAAACAAGGNATGGGATGCCTGATAACACTA
CANCTTCTTTTGAACCTANAANGGTCAAAACACTNCGCTGATGTCACCGGTTCTCAGTCN
CGCGANACACGGAGGAAACANAGGCGATGGTCCGNGTNCAGTAGTAANGGCACTTAACAT
GCAGNTTNTTTAACCTCGGGGCCNCCAGCCCTCCANAGGGCCT

Fig. 2 mine16328human_s2
AATTTGGCCCTCGAGGCCAANAATTCGGCACGAGGACATAAGCCACCAATCCCTGAAAGA
TTAAGCCCTGAAGGAAAGGACTTCCTTTCTCACTGCCTTGAGAGTGACCCAAAGATGAGA
TGGACCGCCAGCCAGCTCCTCGACCATTCGTTTGTCAAGGTTTGCACAGATGAAGAATGA
AGCCTAGTAGAATATGGACTTGGAAAATTCTCTTAATCACTACTGTATGTAATATTTACA
TAAAGACTGTGCTGAGAAGCAAGTATAAGCCCTTTTTAACCTTCCAAGNACTGANGACTG
CACAGGTGACAAGCCGTCACTTNTCCTGCTGCTCCTGTTTTGCCTGNATGTTGGCAAAAA
NGCCCTCTGGAAGG

Fig. 3 mine16358human_c1
GGGGTGCACCATGCTGGCCATAGGGGTGGGGAGAGAGCCAGGCGTCAGGGAGCCTGCCGC
TTTGAGCAGGCCAGACAGCAGGGGATCAGGTTTCAGCCCAGCTTGTATTTTTGGCTGGGT
GGGCTGGGGGCCGAACAGGCAGCGTCAGCTGCCCATCCCCAGCACACACCACACTCACAC
TACCTTTACCCAGATAGGGCACCATCCACTGCCCCCACCCCCCCAGCCCCCTGCAGGCAG
AAAGGAATCAGGTGCTCCTGGGCTATTGAATNACTTTAGGNTTTNTTGGACTGTGGCTAA
TTTTTTGGAAGGNCTTCTTGATCCGCAACGCNGGTGAGNNNGGCAGAGGGGTTTGGNTAC
CAGNACTCCCGCATNATNTNANGCTAGNGCCTGAGANGACCCGGGTCTGCNACCAACCCG
GTTTAGGGATGGGGGGGGGTCTGTTGANTCCNCACACNCCACCTTNTTTATGTCCTCAAA
GGCTGGGGTCNTTGGGCCACCACATTNNTACAAAGGGGTNGGTCTATAANTCCTCCCNCG
AATGC

Fig. 4 mine16676human_s1
CGCGTCCGAGCAGTGCCCTCNAGGATCCTGAAGCAGTACAGCCACCCCAACATCGTGCGT
CTCATTGGTGTCTGCACCCAGAAGCAGCCCATCTACATCGTCATGGAGCTTGTGCAGGGG
GGCGACTTCCTGACCTTCCTCCGCACGGAGGGGGCCCGCCTGCGGGTGAAGACTCTGCTG
CAGATGGTGGGGGATGCAGCTGCTGGCATGGAGTACCTGGAGAGCAAGTGCTGCATCCAC
CGGGACCTGGCTGCTCGGAACTGCCTGGTGACAGAGAAGAATGTCCTGAAGAATCAGTGA
CTTTGGGGATGTCCCGAGAGGAAGCCCGATTGGGGGTCTATGCAGCCTCAGGGGCCTCA
G

Fig. 5 mine16692human_c1
GATGGTTTATTCCAAAGCTGTGGACGGTGAACATTAAGACGAAAGAGGTGACTCGCGTGG
AACCTGAAACACGGACGCCTTTCTTCCAAGAAGGGCTGTGGCGATCAGGCCACTCAAGGC
AGCCAGCCCCTCAGCAGGGCACGATGGCTAATGCTGCCTGGACCGCAGGACTTTTGTTC
GATTTCAAGACACCAGACTCCCTCTCCTTCTCAGGGTCGAAGACTTCTGGATGAGGAGGC
TGTGACAGATATTGCAGATCTTCACCGCGTCGGGGTACGTCTCCCGGATGTATTGCTCCA
TCTCCAGGATGGCCCGGCCGTGCAGGGTGAACTCCCCTTCCTTCTCAATCAGCCACTTGT
TTTGAACAAACTTCTGCAGCACCTGCTCCGCTTCCTTCTTCCTCATCTTCTTGCCTTTAA
GTTGATCAACCAGGTTCAATATGTTTGTGGAAGACGCAAAGCCGGTT

Fig. 6 mine16692human_c2
AAGGGAATAAGCTTGCGGCCGCATCTNNTTTNNNTNNNNNTTTNTTTTTTTTTTTTTTT
TTGCAGCAACTTCCCAGGATGGTTTATTCCAAAGCTGTGGACGGTGAACATTAAGACGAA
AGAGGTGACTCGCGTGGAACCTGAAACACGGACGCCTTTCTTCCAAGAAGGGCTGTGGCG
ATCAGGCCACTCAAGGCAGCCAGCCCCTCAGCAGGGCACGATGGCTAATGCTGCCTGGAC
CGCAGGGACTTTTTGTTCGATTTCAAGACACCAGACTCCCTCTCCTTCTCAGGGTCGAAG
ACTTTTGGGATCTCGTGGGGCCAGTAGTCGTTGCAGTGGGGCAGCGCGGTTCAGCATTC
GACTGGAAGTACTTGGCCACGCAGGGTAAGTGCATCCTGATCCCACAGGTTTCGCAGCTT
TGACCCTGGATGAGGAGGCTGTGACAGATATTGCAGATCTTCACCGCGTCGGGGTACGTC
TCCCGGATGTATTGCTCCATCTCCAGGATGGCCCGGCCGTGCAGGGTGAACTCCCCTTCC
TTCTCAATCAGCCACTTGTTTTGAACAAACTTCTGCAGCACCTGCTCCGCTTCCTTCTTC
CTCATCTTCTTGCCTTTAAGTTGATCAACCAGGTTCAATATGTTTGTGGAAGACGCAAAG
CCGGTTTCTGAGTCAATAATCAGTTCCAGAGCCTTTCTAAACAAATCCAGTTCATTCTCT
GCAAAATCCGTAGCCATTTTGGAAATTGAAGTTGTAGCAAGATTCACCAACGCATAAATG
GGTCTCCCATCATCTTCCGTGACTCCTCTCTTTATCTCAATATACAAGGACTCCAAGACA
CTGTTAATGTTGTTGATGAAGTCCTCCAACTTATCTACGGTGGCATTGCGGTCATGGACC
TTGTAGCAGTGCGTCTGCAAGCGCTTCACGTCCCATTCCTCTAGCACGCCATGGGTCATC
AGCAACTGGAGGAAGCGCCGGTGGACATCAGTCATGACGCCCATTCTCCTTGTGCTGCCC
TGCATGTGGGAACGAACAGGGAGCCCAAGCGCATCCCAGGCCGCGCTAGCGGATACGGCC
TCGAGGCTGTAACATAAGCGGCTGCGGACTTGTACAAAGTAAGAAACTCCGTACACAAA
CAGAGGGGAGCACGGAGGGCGGCGGGACAAAGAGGGTGGTCGGCAAAGGCTGTATTTTCC
ATAGATGTAATCACAGTTTGAATCGAAATACAACTACTCCTTCCTCACCACTCAGCCCAA
GCGCACCCCA

Fig. 7 mine23552human_cl
CGCGTCCGCGCGGTGTATGCTGAGCCGCTGCCGCAGCGGGCTGCTCCACGTCCTGGGCCT
TAGCTTCCTGCTGCAGACCCGCCGGCCGATTCTCCTCTGCTCTCCACGTCTCATGAAGCC
GCTGGTCGTGTTCGTCCTCGGCGGCCCCGGCGCCGGCAAGGGGACCCAGTGCGCCCGCAT
CGTCGAGGAAATGGATCAGACAATGGCTGCCAATGCTCAGAAGAATAAATTCTTGATTGA
TGGGTTTCCAAGAAATCAAGACAACCTTCAAGGATGGAACAAGACCATGGATGGGAAGGC
AGATGTATCTTTCGTTCTCTTTTTTGACTGTAATAATGAGATTTGTATTGAACGATGTCT
TGAGAGGGGAAGAGTAGTGGTGNNANTTGGATGACAACANAGAGAGCTTGGAAAAGAGA
ATTCAGNCCTACCTTCAGNCAACAAAGCCAATTTATTGACTTATATTGAAGAA

Fig. 8 mine23552human_c2
CGGCGCCGGCTCAGCCCGCCCCTTTCTCCCGCCGCCTCCCCGCCCCGCCCCGCGCCGCGC
CGGCCGCTGTCAGCTCCCTCAGCGTCCGGCCGAGGCGCGGTGTATGCTGAGCCGCTGCCG
CAGCCGGCTGCTCCACGTCCTGGGCCTTAGCTTCCTGCTGCAGACCCGCCGGCCGATTCT
CCTCTGCTCTCCACGTCTCATGAAGCCGCTGGTCGTGTTCGTCCTCGGCGGCCCCGGCGC
CGGCAAGGGGACCCAGTGCGCCCGCATCGTCGAGAAATATGGCTACACACACCTTTCTGC
AGGAGAGCTGCTTCGTGATGAAAGGAAGAACCCAGATTCACAGTATGGTGAACTTATTGA
AAAGTACATTAAAGAAGGAAAGATTGTACCAGTTGAGATAACCATCAGTTTATTAAAGAG
GGAAATGGATCAGACAATGGCTGCCAATGCTCAGAAGAATAAATTCTTGATTGATGGGTT
TCCAAGAAATCAAGACAACCTTCAAGGATGGAACAAGACCATGGATGGGAAGGCAGATGT
ATCTTTCGTTCTCTTTTTTGACTGTAATAATGAGATTTGTATTGAACGATGTCTTGAGAG
GGGAAAGAGTAGTGGTAGGAGTGATGACAACAGAGAGAGCTTGGAAAAGAGAATTCAGAC
CTACCTTCAGTCAACAAAGCCAATTATTGACTTATATGAAGAAATGGGGAAAGTCAAGAA
AATAGATGCTTCTAAATCTGTTGATGAAGTTTTTGATGAAGTTGTGCAGATTTTGACAA
GGAAGGCTAATTCTAAACCTGAAAGCATCCTTGAAATCATGCTTGAATATTGCTTTGATA
GCTGCTATCATGACCCCTTTTTAAGGCAATTCTAATCTTTCATAACTACATCTCAATTAG
TGGCTGGAAAGTACATGGTAAAACAAAGTAAATTTTTTATGTTCTTTTTTTTGGTCACA
GGAGTAGACAGTGAATTCAGGTTTAACTTCACCTTAGTTATGGTGCTCACCAAACGAAGG
GTATCAGCTATTTTTTTTAAATTCAAAAGAATATCCCTTTTATAGTTTGTGCCTTCTG
TGAGCAAAACTTTTTAGTACGCGTATATATCCCTCTAGTAATCACAACATTTTAGGATTT
AGGGATACCTGCTTCCTCTTTTTCTTGCAAGTTTTAAATTTCCAACCTTAAGTGAATTTG
TGGACCAAATTTCAAAGGAACTTTTTGTGTAGTCAGTTCTTGCACAATGTGTTTGGTAAA
CAAACTCAAAATGGATTCTTAGGAGCATTTAGTGTTTATTAAATAACTGACCATTTGCT
GTAGAAAGATGAGAAAACTTAAGCTTTGTTTTACTACAACTTGTACAAAGTTGTATGACA
GGGCATATTCTTTGCTTCCAAGATTTGGGTTGGGGCACTAGGGGTTCAGAGCCTGGCAG
AATTGTCAGCTTTAGTCTGACATAATCTAAGGGTATGGGCAAGGATCACATCTAATGCT
TGTGTTCCTTATACTCTATTATATAGTGTTATTCATGATTCAGCTGATCTTAACAAAATT
CGTAGCAGTGGAACCTTGAAATGCATGTGGCTAGATTTATGCTAAAATGATTCTCAGTTA
GCATTTTAGTAACACTTCAAAGGTTTTTTTTGTTTGTTTTCTAGACTTAATAAAAGCTT
AGGATTAATTAGAAGAAGCAATCTAGTTAAATTTCCCATTTGTATTTATTTTCTTGAAT
ACTTTTTTCATAGTTATTTGTTTAAAAAGATTTAAAAATCATTGCACTTTGGTCAGAAAA
ATAATAAATATATCTTATAAATGTTTGATTCCCTTCCTTGCTATTTTATTCAGTAGATT
TTTGTTTGGCATCATGTTGAAGCACCGAAAGATAAATGATTTTAAAAGGCTATAGAGTC
CAAAGGAATATTCTTTTACACCAATTCTTCCTTTAAAAATCTCTGAGGAATTTGTTTTCG
CCTTACTTTTTTTTCTTCTGTCACAATGCTAAGTGGTATCCGAGGTTCTTAATATGAGAT
TTAAAATCTTAAAATGTTTCTTATTTTCAGCACTTACATCATTTGGTACACAGGGTCAAA
TAGGGCAAATAATTTTGTCTTTGTATAATAGATTTGATATTTAAAGTCACTGGAAATAGG
ACAAGTTAATGGATGTTTTTATATTTTAATAGAATCATTTATTTCTATGTGTTATGAAAT
TCACTTAATGATAAATTTTTCAACATACTTGCCATTAGAAAACAAAGTATTGCTAAGTAC
TATAACATATTGGCCACTAAAATTCATATTGAGATTATCTTGGTTTCTTGGAAGAGATAG
GAATGAGTTCTTATCTAGTGTTGCAGGCCAGCAAATACAGAGGTGGTTTAATCAAACAGC
TCTAGTATGAAGCAAGAGTAAAGACTAAGGTTTCGAGAGCATTCCTACTCACATAAGTGA
AGAAATCTGTCAGATAGGAATCTAAATATTTATAGTGAGATTGTGAAAGCAACCTTAAAG
TTTTGAAGAAGACTGATGAGACTAGGTGCTTTGCTTCCTTTCATCAGGTATCTTTCTGTG
GCATTTGAGAACAGAAACCAAGAACATGGTAATTACTAAATTATGAGGCTTTGCTTTTT
GTTTGCTTTTAAGTAGAAAAACATGTTGGCAACATTGAGTTTTGGAGTTGATTGAGATAA
TATGACTTAACTAGTTTTGTCATTCCATTTGTTAAAGATACAGTCACCAAGAATGTTTTG
AGTTTTTTGAAAGACCCCAATTTAAGCCTTGCTTATTTTAAATTATTTCCATTCAGTGA
TGTTGGATGTATATCAGTTATTTAGTAAATAATCTCAATAAATTTTGTGCTGTGGCCTTT
GCTAAAAAAAAAAAAAAATATTGGTGACTGTATCTTTAACAAATGGAATGACAAAACTAG
TTAAGTCATATTATCTCAATCAACTCCAAAACTCAATGTTGCCAACATGTTTTTCTACTT
A

Fig. 9 mine32641human_s1
NCNCGTCCGGTGACCTGAAGTCGGACAACATTCTGGTGTGGTCCCTTGACGTCAAGGAGC
ACATCAACATCAAGCTATCTGACTACGGGATTTCGAGGCAGTCATTCCATGAGGGCGCCC
TAGGCGTGGAGGGCACTCCTGGCTACCAGGCCCCAGAGATCAGGCCTCGCATTGTATATG
ATGAGAAGGTAGATATGTTCTCCTATGGAATGGTGCTCTACGAGTTGCTGTCAGGACAGC
GCCCTGCACTGGGCCACCACCAGCTCCAGATTGCCAAGAAGCTGTCCAAGGGCATCCGCC
CGGTTCTGGGGCAGCCGGAGGAAGTGCAGTTCCGGCGACTGCAGGCGCTCATGATGGAGT
GCTGGGACACTAAGCCAGAGAAGCGACCACTGGCCCTGTCGGTGGTGAAGCCAGATGAAG
GACCCGACTTTTGCCACCTTCATGTATGAACTGTGCTGTGGGAAGCAGACAGCCTTCTTC
TTCATNCCAGGGCCAGGAGTACACTGTGGGTGTTTTGGGATGGAAA

Fig. 10 mine42960human_c1
TTTTTTTTTTCAATAACAAAGGTCCAGTATTACCCACAACAAAGACAAATATTTTCAACA
TAGAACAATAAGAGATATTGATACCCTATGAGCTTGTTACATCTCTGTCATTTTACACAT
TGAGATCAAAATCCAAACACCAGGAGGCCCTCTGGTAAAAGAGTGCTGGCTGCCTACCCA
ACATTCTCCCCTAATGTCTTAGTGTCAGAACCCCTTTGTTATTAGGGATAGTCACGTACC
CAGCAAATAAGCCACATCTCCCAGCCTCCATTCCAGGTAGGGGTGGGTGGTTAGTGAGAT
GGAAGCAGAAGTCATTGGGTGGAGCTTTTGGGAAAGCTCTTTAAAAGCGCCCTTTGCTCT
TCTCCCCTTTCCTCCATTTTCCCTTCCCTAAACACAAAATAGGCAGCTAGAGCTCCAGTA
ACCATCTTGTAGCAAACCTAACATTGGAAGCCATTTGTCAAGGTTGGCAGGGCAGAGATA
CAGCCTCTGAGTATCTGATGACCTGTCCTGCCAGTCCTGGACTCCGAAACATTATTTTTC
TTTTATGTGCTGGAAAAAATAAACCTGCTTCTCGTTGAAGCCATTGNTAGTTTGAGTCGC
TCTTCCTAGCAGCTGAAGGTAATTCCTTACTAATACCAGCTGGCCTCAGTAGTTTCACAG
GTCCTTCCGGACGCGGGGTCGAC

Fig. 11 mine43043human_cl
TCAGATCCCAATCTCCCCCCAAGTATCTCGTCACAAATCACACTATCGTAATCGAGAACA
CTTTGCTACTATACGGACAGCATCACTGGTTACGAGGCAAATGCAAGAACATGAGCAGGA
CTCTGAGCTTAGAGAACAAATGTCTGGCTATAAGCGGAATGAGGCGACAACATCAAAAGC
AACTGATGNCTCTGGAAAACAAGCTAAAGGCTGAGATGGATGAACATCGCCTCAGATTAG
ACAAAGATCTTGAAACTCAGCGTAACAATTTTGCTGCAGAAATGGAGAAACTTATCAAGA
AACACCAGGCTGCTATGGAGAAGAGGCTAAAGTGATGTCCAATGAAGAGAAAAAATTTC
AGCAACATATTCAGGCCCAACAGAAGAAGAACTGAATAGTTTTCTCGAGTCCCAGAAAA
GAGAGTATAAACTTCGAAAAGAGCAGCTTAAAGAGGAGCTAAATGAAAACCAGAGTACCC
CCAAAAAAGAAAAACAGGAGTGGCTTTCAAAGCAGAAGGAGAATATACAGCATTTCCAAG
CAGAAGAAGAAGCTACCTTCTTCGACGTCAAGACAATACCTAGAGCTGGAATGCCCGTC
GCTTCAAGAGAAGAATGTTACTTGGGCGTCATAACTTAGAGCAGGACCTTGTCAGGGAGG
AGTTAAACAAAGACAGACTCAGAAGGACTTAGAGCATGCCATGCTACTCCGACAGCATG
AATCTATGCAAGAACTGGAGTTCGCCACCTCAACACAATTCAGAAGATGCGCTGTGAGT
TGATCAGATTACAGCATCAAACTGAGCTCACTAACCAGCTGGAATATAATAAGCGAAGAG
AACGAGAACTAAGACGAAAGCATGTCATGGAAGTTCGACAACAGCCTAAGAGTTTGAAGT
CTAAAGAACTCCAAATAAAAAAGCAGTTTCAGGATACCTGCAAAATCCAAACCAGACAGT
ACAAAGCATTAAGAAATCACCTGCTGGAGACTACACCAAAGAGTGAGCACAAAGCTGTTC
TGAAACGGCTCAAGGAGGAACAGACCCGGAAATTAGCTATCTTGGCTGAGCAGTATGATC
ACAGCATTAATGAAATGCTCTCCACACAAACCGTGGGTTTGCTTTTTTTGGGGCAAAACA
AATTTAGTGCCCCTTTTCTTCCCCCACCTGAACGAAATCACAGCAATTAAAGTACTAGTT
GGAAATGATAGCTCTCCCGAGCTTATCAAAAAAAAAAAAAAAAAAAAAAAAAAAAAAAAAC
AACATGGTGAAACCCTGTCTCTGCTGAAAGTACAAAAATTAGTTGGGTGTGGCGGCACAT
GCCTGTGGTCCCAGCTACTCGGGGGGCTGAAGCAGGAGAATCCCTTGAACCCAGGAGGCA
GAGGTTGCAGTGAGTCAAGAACACACCACAGCACTCCAGCCCGGGTGACAGAGCAAGACC
CTGTCTCA

Fig. 12 mine42957human_cl
TCTCGGCCCGGCTGCGCCAGAGTCCGCGCGATGGAGCCCCGGCCGCGGCGGCGGCGCAGG
AGTCGCCCCCTGGTCGCCGCCTTCCTGCGAGACCCGGGCTCGGGCCGCGTGTACAGGCGC
GGGAAGCTGATCGGCAAGGGCGCCTTCAGCCGCTGCTACAAGCTGACAGACATGTCCACC
AGCGCCGTGTTCGCCCTCAAGGTGGTGCCGTGTGGCGGGGCTGGGGCCGGGTGGCTTCGC
CCGCAGGGAAAGGTGGAGCGTGAGATTGCCCTGCATAGCCGCCTGCGACCCCGCAACATC
GTGGCTTTCCACGGACACTTTGCTGACCGCGACCACGTGTACATGGTGCTGGAGTACTGC
AGCCGCCAGTCTTTGGCCCACGTGCTGAGGGCGCGGCAGATCCTGACGGAGCCAGAAGTG
CGCGACTACCTGCGGGGCCTGGTCAGCGGCCTGCGCTACCTGCACCAGCGGTGCATCCTG
CACCGCGACCTGAAGCTCAGTAACTTCTTCCTTAACAAGAA

Fig. 13 mine42958human_sl
GGCTGATTTTGGTCTTGCCCGGGCCAAGTCCATTCCCAGCCAGACATACTCTTCAGAAGT
CGTGACCCTCTGGTACCGGCCCCCTGATGCTTTGCTGGGAGCCACTGAATATTCCTCTGA
GCTGGACATATGGGGTGCAGGCTGCATCTTTATTGAAATGTTCCAGGGTCAACCTTTGTT
TCCTGGGGTTTCCAACATCCTTGAACAGCTGGAGAAAATCTGGGAGGTGCTGGGAGTCCC
TACAGAGGATACTTGGCCGGGAGTCTCCAAGCTACCTAACTACAATCCAGAATGGTTCCC
ACTGCCTACGCCTCGAAGCCTTCATGTTGTCTGGAACAGGCTGGGCAGGGTTCCTGAAGC
TGAAGACCTGGCCTCCCAGATGCTAAAAGGCTTTCCCAGAGACCGCGTCTCCGCCCAGGA
AGCACTTGTTCATGATTATTTCAGCGCCCTGCCATCTCAGCTGTACCAGCTTCCTGATGA
G

Fig. 14

NUCLEIC ACID MOLECULES ENCODING HUMAN KINASE AND PHOSPHATASE HOMOLOGUES AND USES THEREFOR

BACKGROUND OF THE INVENTION

Phosphate tightly associated with a molecule, e.g., a protein, has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated molecules, e.g., proteins implies the existence of one or more kinases, e.g., protein kinases, capable of phosphorylating various molecules, e.g., amino acid residues on proteins, and also of phosphatases, e.g., protein phosphatases, capable of hydrolyzing various phosphorylated molecules, e.g., phosphorylated amino acid residues on proteins.

Protein kinases and phosphatases play critical roles in the regulation of biochemical and morphological changes associated with cellular growth and division (D'Urso, G. et al. (1990) *Science* 250: 786–791; Birchmeier. C. et al. (1993) *Bioassays* 15: 185–189). They serve as growth factor receptors and signal transducers and have been implicated in cellular transformation and malignancy (Hunter, T. et al. (1992) *Cell* 70: 375–387; Posada, J. et al. (1992) *Mol. Biol. Cell* 3: 583–592; Hunter, T. et al. (1994) *Cell* 79: 573–582). For example, protein kinases have been shown to participate in the transmission of signals from growth-factor receptors (Sturgill, T. W. et al. (1988) *Nature* 344: 715–718; Gomez, N. et al. (1991) *Nature* 353: 170–173), control of entry of cells into mitosis (Nurse, P. (1990) *Nature* 344: 503–508; Maller, J. L. (1991) *Curr. Opin. Cell Biol.* 3: 269–275) and regulation of actin bundling (Husain-Chishti, A. et al. (1988) *Nature* 334: 718–721).

Protein kinases and phosphatases can be divided into different groups based on either amino acid sequence similarity or specificity for either serine/threonine or tyrosine residues. A small number of dual-specificity kinases and phosphatases have also been described. Within the broad classification, kinases and phosphatases can be further subdivided into families whose members share a higher degree of catalytic domain amino acid sequence identity and also have similar biochemical properties. Most protein kinase and phosphatase family members also share structural features outside the kinase and phosphatase domain, respectively, that reflect their particular cellular roles. These include regulatory domains that control kinase or phosphatase activity or interaction with other proteins (Hanks, S. K. et al. (1988) *Science* 241: 42–52).

SUMMARY OF THE INVENTION

The present invention is based, at least in part, on the discovery of novel nucleic acid molecules and polypeptides encoded by such nucleic acid molecules, referred to herein as "Kinases" and "Phosphatases". The Kinase and Phosphatase nucleic acid and polypeptide molecules of the present invention are useful as modulating agents in regulating a variety of cellular processes. Accordingly, in one aspect, this invention provides isolated nucleic acid molecules encoding Kinase and Phosphatase polypeptides, as well as nucleic acid fragments suitable as primers or hybridization probes for the detection of Kinase- and Phosphatase-encoding nucleic acids.

In one embodiment, a Kinase and a Phosphatase nucleic acid molecule of the invention is at least 60%, 65%, 70%, 75%, 80%, 85%, 90%, 95%, 98% or more homologous to a nucleotide sequence (e.g., to the entire length of the nucleotide sequence) including SEQ ID NO:1–14, or a complement thereof.

In a preferred embodiment, the isolated nucleic acid molecule includes the nucleotide sequence shown SEQ ID NO:1–14, or a complement thereof. In another preferred embodiment, an isolated nucleic acid molecule of the invention encodes the amino acid sequence of a human Kinase or Phosphatase polypeptide.

Another embodiment of the invention features nucleic acid molecules, preferably Kinase and Phosphatase nucleic acid molecules, which specifically detect Kinase and Phosphatase nucleic acid molecules relative to nucleic acid molecules encoding non-Kinase and non-Phosphatase polypeptides. For example, in one embodiment, such a nucleic acid molecule is at least 20, 30, 40, 50, 100, 150, 200, 250, 300, 350, 400, 450, 500, 550, 600, 650, 700, 750, or 800 nucleotides in length and hybridizes under stringent conditions to a nucleic acid molecule comprising the nucleotide sequence shown in SEQ ID NO:1–14, or a complement thereof.

In other preferred embodiments, the nucleic acid molecule encodes a naturally occurring allelic variant of a human Kinase or Phosphatase polypeptide, wherein the nucleic acid molecule hybridizes to a nucleic acid molecule which includes SEQ ID NO: 1–14 under stringent conditions.

Another embodiment of the invention provides an isolated nucleic acid molecule which is antisense to a Kinase or a Phosphatase nucleic acid molecule, e.g., the coding strand of a Kinase or a Phosphatase nucleic acid molecule.

Another aspect of the invention provides a vector comprising a Kinase or a Phosphatase nucleic acid molecule. In certain embodiments, the vector is a recombinant expression vector. In another embodiment, the invention provides a host cell containing a vector of the invention. The invention also provides a method for producing a polypeptide, preferably a Kinase or a Phosphatase polypeptide, by culturing in a suitable medium, a host cell, e.g., a mammalian host cell such as a non-human mammalian cell, of the invention containing a recombinant expression vector, such that the polypeptide is produced.

Another aspect of this invention features isolated or recombinant Kinase polypeptides and proteins. In one embodiment, the isolated polypeptide, preferably a Kinase polypeptide, is a eukaryotic protein kinase. Another aspect of this invention features isolated or recombinant Phosphatase polypeptides and proteins.

In a further embodiment, the isolated polypeptide, preferably a Kinase or a Phosphatase polypeptide, plays a role in signaling pathways associated with cellular growth, e.g., signaling pathways associated with cell cycle regulation. In another embodiment, the isolated polypeptide, preferably a Kinase or a Phosphatase polypeptide is encoded by a nucleic acid molecule having a nucleotide sequence which hybridizes under stringent hybridization conditions to a nucleic acid molecule comprising the nucleotide sequence of SEQ ID NO:1–14.

Another embodiment of the invention features an isolated polypeptide, preferably a Kinase and a Phosphatase polypeptide, which is encoded by a nucleic acid molecule having a nucleotide sequence at least about 50%, 55%, 60%, 65%, 70%, 75%, 80%, 85%, 90%, 95%, 98% or more homologous to a nucleotide sequence (e.g., to the entire length of the nucleotide sequence) including SEQ ID NO:1–14 or a complement thereof.

This invention further features an isolated polypeptide, preferably a Kinase and a Phosphatase polypeptide, which is encoded by a nucleic acid molecule having a nucleotide sequence which hybridizes under stringent hybridization conditions to a nucleic acid molecule comprising the nucleotide sequence of SEQ ID NO:1–14, or a complement thereof.

In another aspect, the invention pertains to any individual Kinase or Phosphatase nucleic acid molecule from the above-identified group (SEQ ID NO:1–14), as well as any subgroups from within the above-identified group. Furthermore, the subgroups can preferably consist of at least 1, 5, 10, or more members of the group identified above. For example, the group consisting of the Kinase and Phosphatase nucleic acid molecules of SEQ ID NO:1–14 can be divided into one or more subgroups as follows: SEQ ID NO:1–4, SEQ ID NO:4–8, SEQ ID NO:8–12, and SEQ ID NO:12–14, or any combinations thereof.

The polypeptides of the present invention can be operatively linked to a non-Kinase and a non-Phosphatase polypeptide (e.g., heterologous amino acid sequences) to form fusion proteins. The invention further features antibodies, such as monoclonal or polyclonal antibodies, that specifically bind polypeptides of the invention, preferably Kinase and Phosphatase polypeptides. In addition, the Kinase and Phosphatase polypeptides, e.g., biologically active polypeptides, can be incorporated into pharmaceutical compositions, which optionally include pharmaceutically acceptable carriers.

In another aspect, the present invention provides a method for detecting the presence of a Kinase and a Phosphatase nucleic acid molecule, polypeptide or polypeptide in a biological sample by contacting the biological sample with an agent capable of detecting a Kinase and Phosphatase nucleic acid molecule, polypeptide or polypeptide such that the presence of a Kinase and a Phosphatase nucleic acid molecule, polypeptide or polypeptide is detected in the biological sample.

In another aspect, the present invention provides a method for detecting the presence of Kinase and Phosphatase activity in a biological sample by contacting the biological sample with an agent capable of detecting an indicator of Kinase and Phosphatase activity such that the presence of Kinase and Phosphatase activity is detected in the biological sample.

In another aspect, the invention provides a method for modulating Kinase and Phosphatase activity comprising contacting a cell capable of expressing Kinase and Phosphatase with an agent that modulates Kinase and Phosphatase activity such that Kinase and Phosphatase activity in the cell is modulated. In one embodiment, the agent inhibits Kinase and Phosphatase activity. In another embodiment, the agent stimulates Kinase and Phosphatase activity. In one embodiment, the agent is an antibody that specifically binds to a Kinase and Phosphatase polypeptide. In another embodiment, the agent modulates expression of Kinase and Phosphatase by modulating transcription of a Kinase and Phosphatase gene or translation of a Kinase and Phosphatase mRNA. In yet another embodiment, the agent is a nucleic acid molecule having a nucleotide sequence that is antisense to the coding strand of a Kinase or Phosphatase mRNA or a Kinase or Phosphatase gene.

In one embodiment, the methods of the present invention are used to treat a subject having a disorder characterized by aberrant Kinase or Phosphatase polypeptide or nucleic acid expression or activity by administering an agent which is a Kinase or a Phosphatase modulator to the subject. In one embodiment, the Kinase and Phosphatase modulator is a Kinase and a Phosphatase polypeptide, respectively. In another embodiment the Kinase and Phosphatase modulator is a Kinase and Phosphatase nucleic acid molecule, respectively. In yet another embodiment, the Kinase and Phosphatase modulator is a peptide, peptidomimetic, or other small molecule. In a preferred embodiment, the disorder characterized by aberrant Kinase or Phosphatase polypeptide or nucleic acid expression is a cellular growth related disorder, e.g., a proliferative disorder such as cancer.

The present invention also provides a diagnostic assay for identifying the presence or absence of a genetic alteration characterized by at least one of (i) aberrant modification or mutation of a gene encoding a Kinase or a Phosphatase polypeptide; (ii) mis-regulation of the gene; and (iii) aberrant post-translational modification of a Kinase or a Phosphatase polypeptide, wherein a wild-type form of the gene encodes a polypeptide with a Kinase or a Phosphatase activity.

In another aspect the invention provides a method for identifying a compound that binds to or modulates the activity of a Kinase or a Phosphatase polypeptide. The method includes providing an indicator composition comprising a Kinase or a Phosphatase polypeptide having Kinase or Phosphatase activity, respectively, contacting the indicator composition with a test compound, and determining the effect of the test compound on Kinase or Phosphatase activity in the indicator composition to identify a compound that modulates the activity of a Kinase or a Phosphatase polypeptide.

Other features and advantages of the invention will be apparent from the following detailed description and claims.

BRIEF DESCRIPTION OF THE DRAWINGS

FIG. 1 depicts a human cDNA sequence designated 14803C1 (SEQ ID NO:1).

FIG. 2 depicts a human cDNA sequence designated 16328S1 (SEQ ID NO:2).

FIG. 3 depicts a human cDNA sequence designated 16328S2 (SEQ ID NO:3).

FIG. 4 depicts a human cDNA sequence designated 16358C1 (SEQ ID NO:4).

FIG. 5 depicts a human cDNA sequence designated 16676S1 (SEQ ID NO:5).

FIG. 6 depicts a human cDNA sequence designated 16692C1 (SEQ ID NO:6).

FIG. 7 depicts a human cDNA sequence designated 16692C2 (SEQ ID NO:7).

FIG. 8 depicts a human cDNA sequence designated 23552C1 (SEQ ID NO:8).

FIG. 9 depicts a human cDNA sequence designated 23552C2 (SEQ ID NO:9).

FIG. 10 depicts a human cDNA sequence designated 32641S1 (SEQ ID NO:10).

FIG. 11 depicts a human cDNA sequence designated 42960C1 (SEQ ID NO:11).

FIG. 12 depicts a human cDNA sequence designated 43043C1 (SEQ ID NO:12).

FIG. 13 depicts a human cDNA sequence designated 42957C1 (SEQ ID NO:13).

FIG. 14 depicts a human cDNA sequence designated 42958S1 (SEQ ID NO:14).

DETAILED DESCRIPTION OF THE INVENTION

I. Isolated Nucleic Acid Molecules —10
II. Isolated Kinase and Phosphatase Proteins and Anti-Kinase and Anti-Phosphatase Antibodies —19
III. Recombinant Expression Vectors and Host Cells —29
IV. Pharmaceutical Compositions —37
V. Uses and Methods of the Invention —40
   A. Screening Assays —41
   B. Detection Assays —47
      1. Chromosome Mapping —48
      2. Tissue Typing —50
      3. Use of Partial Kinase and Phosphatase Sequences in Forensic Biology —51
   C. Predictive Medicine —51
      1. Diagnostic Assays —52
      2. Prognostic Assays —54
      3. Monitoring of Effects During Clinical Trials —59
   D. Methods of Treatment —60
      1. Prophylactic Methods —60
      2. Therapeutic Methods —61
      3. Pharmacogenomics —62

The present invention is based, at least in part, on the discovery of novel molecules, referred to herein as "Kinase" and "Phosphatase" nucleic acid and polypeptide molecules, which play a role in or function in signaling pathways associated with cellular growth and/or cellular metabolic pathways. These growth and metabolic pathways are described in Lodish H. et al. Molecular Cell Biology, (Scientific American Books Inc., New York, N.Y., 1995) and Stryer L., Biochemistry, (W. H. Freeman, New York), the contents of which are incorporated herein by reference. In one embodiment, the Kinase and Phosphatase molecules modulate the activity of one or more proteins involved in cellular growth or differentiation, e.g., cardiac, epithelial, or neuronal cell growth or differentiation. In another embodiment, the Kinase and Phosphatase molecules of the present invention are capable of modulating the phosphorylation state of a Kinase or Phosphatase molecule or the phosphorylation state of one or more proteins involved in cellular growth or differentiation, e.g., cardiac, epithelial, or neuronal cell growth or differentiation, as described in, for example, Lodish H. et al. Molecular Cell Biology, (Scientific American Books Inc., New York, N.Y., 1995) and Stryer L., Biochemistry, (W. H. Freeman, New York), the contents of which are incorporated herein by reference. In addition, Kinases and Phosphatases of the present invention are targets of drugs described in Goodman and Gilman, The Pharmacological Basis of Therapeutics ($9^{th}$ Edition) (Hartman & Limbard Editors, 1996), the contents of which are incorporated herein by reference.

As used herein, the term "Kinase" includes a protein, polypeptide, or other non-proteinaceous molecule which is capable of modulating its own phosphorylation state or the phosphorylation state of a different protein, polypeptide, or other non- proteinaceous molecule. Kinases can have a specificity for (i.e., a specificity to phosphorylate) serine/threonine residues, tyrosine residues, or both serine/threonine and tyrosine residues, e.g., the dual specificity kinases. As referred to herein, Kinases such as protein Kinases, preferably include a catalytic domain of about 200–400 amino acid residues in length, preferably about 200–300 amino acid residues in length, or more preferably about 250–300 amino acid residues in length, which includes preferably 5–20, more preferably 5–15, or preferably 11 highly conserved motifs or subdomains separated by sequences of amino acids with reduced or minimal conservation. Specificity of a Kinase for phosphorylation of either tyrosine or serine/threonine can be predicted by the sequence of two of the subdomains (VIb and VIII) in which different residues are conserved in each class (as described in, for example, Hanks et al. (1988) *Science* 241:42–52) the contents of which are incorporated herein by reference). These subdomains are also described in further detail herein.

As used herein, the term "Phosphatase" includes a protein or polypeptide, e.g., an enzyme, or another non-proteinaceous molecule which is capable of facilitating, e.g., catalyzing, the removal of a phosphate group from, for example, a protein or polypeptide which is phosphorylated. Phosphatases can have a specificity for (i.e. a specificity to dephosphorylate) serine/threonine residues, tyrosine residues, or both serine/threonine and tyrosine residues. As referred to herein, a Phosphatase such as a protein Phosphatase, can preferably include a catalytic domain of at least about 200–400 amino acid residues in length, preferably about 200–300 amino acid residues in length, and more preferably about 250–300 amino acid residues in length, which includes preferably 2–20, more preferably 2–15, or preferably 2–8 highly conserved motifs or subdomains separated by sequences of amino acids with reduced or minimal conservation. Phosphatases can be either soluble or membrane bound (see e.g., Brautigan et al. (1992) *Biochem. biophys. Acta*, 1114:63–77; Charbonneau et al. (1992) *Ann. Rev. Cell Biol.*, 8:463–493; Fisher et al. (1991) *Science*, 253:401–406; and Hunter et al. (1989) *Cell*, 58:1013–1016). Membrane bound Phosphatases typically contain receptor-like extracellular regions connected to the intracellular (catalytic) domains by a short transmembrane segment (Streuli and Saito, (1993) *Adv. Prot. Phosphatases* 7:67–94). The non-transmembrane (cytoplasmic) Phosphatases typically include at least one catalytic domain (Koch et al., (1991) *Science* 252:668–674).

Kinases and Phosphatases play a role in signaling pathways associated with cellular growth. For example, protein Kinases and protein Phosphatases are involved in the regulation of signal transmission from cellular receptors, e.g., growth-factor receptors; entry of cells into mitosis; and the regulation of cytoskeleton function, e.g., actin bundling. Thus, the Kinase and Phosphatase molecules of the present invention may be involved in: 1) the regulation of transmission of signals from cellular receptors, e.g., growth factor receptors; 2) the modulation of the entry of cells into mitosis; 3) the modulation of cellular differentiation; 4) the modulation of cell death; and 5) the regulation of cytoskeleton function, e.g., actin bundling.

Inhibition or over stimulation of the activity of Kinases and Phosphatases involved in signaling pathways associated with cellular growth can lead to perturbed cellular growth, which can in turn lead to cellular growth related disorders. As used herein, a "cellular growth related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., melanoma, prostate cancer, cervical cancer, breast cancer, colon cancer, or sarcoma.

The present invention is based, at least in part, on the discovery of novel molecules, referred to herein as Kinase and Phosphatase protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

One embodiment of the invention features Kinase and Phosphatase nucleic acid molecules, preferably human Kinase and Phosphatase molecules, which were identified based on a consensus motif or protein domain characteristic of a Kinase or Phosphatase family of proteins. (Such families are described below). The Kinase and Phosphatase nucleic acid and polypeptide molecules of the invention are described in further detail in the following subsections.

A. The Eucaryotic Protein Kinase Nucleic Acid and Polypeptide Molecules

In one embodiment, the isolated nucleic acid molecules of the present invention encode eukaryotic protein kinase polypeptides. Eukaryotic protein kinases (described in, for example, Hanks S. K. et al. (1995) *FASEB J.* 9:576–596) are enzymes that belong to an extensive family of proteins which share a conserved catalytic core common to both serine/threonine and tyrosine protein kinases. There are a number of conserved regions in the catalytic domain of protein kinases. One of this regions, located in the N-terminal extremity of the catalytic domain, is a glycine-rich stretch of residues in the vicinity of a lysine residue, which has been shown to be involved in ATP binding. Another region, located in the central part of the catalytic domain, contains a conserved aspartic acid residue which is important for the catalytic activity of the enzyme (Knighton D.R. et al. (1991) *Science* 253:407–414). Two signature patterns have been described for this region: one specific for serine/ threonine kinases and one for tyrosine kinases.

Eukaryotic protein kinase polypeptides of the present invention preferably include one of the following consensus sequences:

[LIV]-G-{P}-G-{P}-[FYWMGSTNH]-[SGA]-{PW}-[LIVCAT]-{PD}-x [GSTACLIVMFY]-x(5,18)-[LIVMFYWCSTAR]-[AIVP]-[LIVMFAGCKR]-K (SEQ ID NO:15) [K binds ATP]

[LIVMFYC]-x-[HY]-x-D-[LIVMFY]-K-x(2)-N-[LIVMFYCT](3) (SEQ ID NO:16) [D is an active site residue]

[LIVMFYC]-x-[HY]-x-D-[LIVMFY]-[RSTAC]-x(2)-N-[LIVMFYC](3) (SEQ ID NO:17) [D is an active site residue]

SEQ ID NOs:1–8, 10–12, 13, and 14, shown in FIGS. 1–8, 10–12, 13, and 14, respectively, are part of cDNAs that encode eukaryotic protein kinase polypeptides.

B. The Adenylate Kinase Nucleic Acid and Polypeptide Molecules

In one embodiment, the isolated nucleic acid molecules of the present invention encode adenylate kinase polypeptides. Adenylate kinase (AK) (described in Schulz G. E. (1987) *Cold Spring Harbor Symp. Quant. Biol.* 52:429–439) is a monomeric enzyme that catalyzes the reversible transfer of MgATP to AMP (MgATP+AMP=MgADP+ADP).

In mammals there are three different isozymes AK1 (or myokinase) which is cytosolic; AK2, which is located in the outer compartment of mitochondria; and AK3 (or GTP:AMP phosphotransferase), which is located in the mitochondrial matrix and which uses MgGTP instead of MgATP.

Several regions of AK family enzymes are well conserved, including the ATP-binding domains. This region includes an aspartic acid residue that is part of the catalytic cleft of the enzyme and is involved in a salt bridge.

It also includes an arginine residue whose modification leads to inactivation of the enzyme. Adenylate kinase polypeptides of the present invention preferably include the following consensus sequence:

[LIVMFYW](3)-D-G-[FYI]-P-R-x(3)-[NQ] (SEQ ID NO:18)

SEQ ID NO:9 shown in FIG. 9 is part of a cDNA that encodes an adenylate kinase polypeptide.

Various aspects of the invention are described in further detail in the following subsections:

I. Isolated Nucleic Acid Molecules

One aspect of the invention pertains to isolated nucleic acid molecules that encode Kinase and Phosphatase proteins or biologically active portions thereof, as well as nucleic acid fragments sufficient for use as hybridization probes to identify Kinase and Phosphatase-encoding nucleic acids (e.g., Kinase and Phosphatase mRNA) and fragments for use as PCR primers for the amplification or mutation of Kinase and Phosphatase nucleic acid molecules. As used herein, the term "nucleic acid molecule" is intended to include DNA molecules (e.g., cDNA or genomic DNA) and RNA molecules (e.g., MRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Kinase and Phosphatase nucleic acid molecule can contain less than about 5kb, 4kb, 3kb, 2kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1–14, or a portion thereof, can be isolated using standard molecular biology techniques and the sequence information provided herein. For example, using all or portion of the nucleic acid sequence of SEQ ID NO:1–14, as a hybridization probe, Kinase and Phosphatase nucleic acid molecules can be isolated using standard hybridization and cloning techniques (e.g., as described in Sambrook, J., Fritsh, E. F., and Maniatis, T. *Molecular Cloning: A Labo-*

*ratory Manual. 2nd, ed.*, Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1–14 can be isolated by the polymerase chain reaction (PCR) using synthetic oligonucleotide primers designed based upon the sequence of SEQ ID NO:1–14, respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to Kinase and Phosphatase nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1–14.

In another preferred embodiment, an isolated nucleic acid molecule of the invention comprises a nucleic acid molecule which is a complement of the nucleotide sequence shown in SEQ ID NO:1–14, or a portion of any of these nucleotide sequences. A nucleic acid molecule which is complementary to the nucleotide sequence shown in SEQ ID NO:1–14, is one which is sufficiently complementary to the nucleotide sequence shown in SEQ ID NO:1–14, respectively, such that it can hybridize to the nucleotide sequence shown in SEQ ID NO:1–14, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 98% or more homologous to the nucleotide sequence (e.g., to the entire length of the nucleotide sequence) shown in SEQ ID NO:1–14, or a portion of any of these nucleotide sequences.

Moreover, the nucleic acid molecule of the invention can comprise only a portion of the nucleic acid sequence of SEQ ID NO:1–14, for example a fragment which can be used as a probe or primer or a fragment encoding a biologically active portion of a Kinase and Phosphatase protein. The nucleotide sequence determined from the cloning of the Kinase and Phosphatase gene allows for the generation of probes and primers designed for use in identifying and/or cloning other Kinase and Phosphatase family members, as well as Kinase and Phosphatase homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1–14, or of a naturally occurring allelic variant or mutant of SEQ ID NO:1–14. In an exemplary embodiment, a nucleic acid molecule of the present invention comprises a nucleotide sequence which is at least 100, 150, 200, 250, 300, 350, 400, 450, 500, 550, 600, 650, 700, 750, or 800 nucleotides in length and hybridizes under stringent hybridization conditions to a nucleic acid molecule of SEQ ID NO: 1–14.

Probes based on the Kinase and Phosphatase nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress a Kinase and Phosphatase protein, such as by measuring a level of a Kinase and Phosphatase-encoding nucleic acid in a sample of cells from a subject e.g., detecting Kinase and Phosphatase mRNA levels or determining whether a genomic Kinase and Phosphatase gene has been mutated or deleted.

A nucleic acid fragment encoding a "biologically active portion of a Kinase and Phosphatase protein" can be prepared by isolating a portion of the nucleotide sequence of SEQ ID NO:1–14, which encodes a polypeptide having a Kinase and Phosphatase biological activity (the biological activities of the Kinase and Phosphatase proteins are described herein), expressing the encoded portion of the Kinase and Phosphatase protein (e.g., by recombinant expression in vitro) and assessing the activity of the encoded portion of the Kinase and Phosphatase protein.

The invention further encompasses nucleic acid molecules that differ from the nucleotide sequence shown in SEQ ID NO:1–14, due to the degeneracy of the genetic code and, thus, encode the same Kinase and Phosphatase proteins as those encoded by the nucleotide sequence shown in SEQ ID NO:1–14. In another embodiment, an isolated nucleic acid molecule of the invention has a nucleotide sequence encoding a Kinase or Phosphatase protein.

In addition to the Kinase and Phosphatase nucleotide sequences shown in SEQ ID NO:1–14, it will be appreciated by those skilled in the art that DNA sequence polymorphisms that lead to changes in the amino acid sequences of the Kinase and Phosphatase proteins may exist within a population (e.g., the human population). Such genetic polymorphism in the Kinase and Phosphatase genes may exist among individuals within a population due to natural allelic variation. As used herein, the terms "gene" and "recombinant gene" refer to nucleic acid molecules which include an open reading frame encoding an Kinase and Phosphatase protein, preferably a mammalian Kinase and Phosphatase protein, and can further include non-coding regulatory sequences, and introns. Such natural allelic variations include both functional and non-functional Kinase and Phosphatase proteins and can typically result in 1–5% variance in the nucleotide sequence of a Kinase and Phosphatase gene. Any and all such nucleotide variations and resulting amino acid polymorphisms in Kinase and Phosphatase genes that are the result of natural allelic variation and that do not alter the functional activity of a Kinase and Phosphatase protein are intended to be within the scope of the invention.

Moreover, nucleic acid molecules encoding other Kinase and Phosphatase family members and, thus, which have a nucleotide sequence which differs from the Kinase and Phosphatase sequences of SEQ ID NO:1–14 are intended to be within the scope of the invention. For example, another Kinase and Phosphatase cDNA can be identified based on the nucleotide sequence of human Kinase and Phosphatase. Moreover, nucleic acid molecules encoding Kinase and Phosphatase proteins from different species, and thus which have a nucleotide sequence which differs from the Kinase and Phosphatase sequences of SEQ ID NO:1–14 are intended to be within the scope of the invention. For example, a mouse Kinase and Phosphatase cDNA can be identified based on the nucleotide sequence of a human Kinase and Phosphatase.

Nucleic acid molecules corresponding to natural allelic variants and homologues of the Kinase and Phosphatase cDNAs of the invention can be isolated based on their homology to the Kinase and Phosphatase nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1–14. In other embodiment, the nucleic acid is at least 30, 50, 100, 150, 200, 250, 300, 350, 400, 450, 500, 550, or 600 nucleotides in length. As used herein, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1–14 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the Kinase and Phosphatase sequences that may exist in the population, the skilled artisan will further appreciate that changes can be introduced by mutation into the nucleotide sequences of SEQ ID NO:1–14, thereby leading to changes in the amino acid sequence of the encoded Kinase and Phosphatase proteins, without altering the functional ability of the Kinase and Phosphatase proteins. For example, nucleotide substitutions leading to amino acid substitutions at "non-essential" amino acid residues can be made in the sequence of a Kinase or Phosphatase protein. A "non-essential" amino acid residue is a residue that can be altered from the wild-type sequence of Kinase and Phosphatase without altering the biological activity, whereas an "essential" amino acid residue is required for biological activity. For example, amino acid residues that are conserved among the Kinase and Phosphatase proteins of the present invention, are predicted to be particularly unamendable to alteration. Furthermore, additional amino acid residues that are conserved between the Kinase and Phosphatase proteins of the present invention and other Kinase and Phosphatase family members are not likely to be amenable to alteration.

Accordingly, another aspect of the invention pertains to nucleic acid molecules encoding Kinase and Phosphatase proteins that contain changes in amino acid residues that are not essential for activity.

An isolated nucleic acid molecule encoding a Kinase and Phosphatase protein homologous to the Kinase and Phosphatase proteins of the present invention can be created by introducing one or more nucleotide substitutions, additions or deletions into the nucleotide sequence of SEQ ID NO:1–14, such that one or more amino acid substitutions, additions or deletions are introduced into the encoded protein. Mutations can be introduced into SEQ ID NO:1–14 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a Kinase and Phosphatase protein is preferably replaced with another amino acid residue from the same side chain family. Alternatively, in another embodiment, mutations can be introduced randomly along all or part of a Kinase and Phosphatase coding sequence, such as by saturation mutagenesis, and the resultant mutants can be screened for Kinase and Phosphatase biological activity to identify mutants that retain activity. Following mutagenesis of SEQ ID NO:1–14, the encoded protein can be expressed recombinantly and the activity of the protein can be determined.

In a preferred embodiment, a mutant Kinase and Phosphatase protein can be assayed for the ability to: 1) regulate transmission of signals from cellular receptors, e.g., growth factor receptors; 2) control entry of cells, e.g., epithelial cells, into mitosis; 3) modulate cellular differentiation; 4) modulate cell death; or 5) regulate cytoskeleton function, e.g., actin bundling.

In addition to the nucleic acid molecules encoding Kinase and Phosphatase proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Kinase and Phosphatase coding strand, or only to a portion thereof. In one embodiment, an antisense nucleic acid molecule is antisense to a "coding region" of the coding strand of a nucleotide sequence encoding Kinase and Phosphatase. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding Kinase and Phosphatase. The term "noncoding region" refers to 5' and 3' sequences which flank the coding region that are not translated into amino acids (i.e., also referred to as 5' and 3' untranslated regions).

Given the coding strand sequences encoding Kinase and Phosphatase disclosed herein, antisense nucleic acids of the invention can be designed according to the rules of Watson and Crick base pairing. The antisense nucleic acid molecule can be complementary to the entire coding region of Kinase and Phosphatase mRNA, but more preferably is an oligonucleotide which is antisense to only a portion of the coding or noncoding region of Kinase and Phosphatase mRNA. For example, the antisense oligonucleotide can be complementary to the region surrounding the translation start site of Kinase and Phosphatase MRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a Kinase and Phosphatase protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an MRNA, to which they have a complementary region. Thus, ribozymes (e.g., hammerhead ribozymes (described in Haselhoff and Gerlach (1988) *Nature* 334:585–591)) can be used to catalytically cleave Kinase and Phosphatase MRNA transcripts to thereby inhibit translation of Kinase and Phosphatase MRNA. A ribozyme having specificity for a Kinase and Phosphatase-encoding nucleic acid can be designed based upon the nucleotide sequence of a Kinase and Phosphatase cDNA disclosed herein (i.e., SEQ ID NO:1–14). For example, a derivative of a Tetrahymena L-19 IVS RNA can be constructed in which the nucleotide sequence of the active site is complementary to the nucleotide sequence to be cleaved in a Kinase and Phosphatase-encoding MRNA. See, e.g., Cech et al. U.S. Pat. No. 4,987,071; and Cech et al. U.S. Pat. No. 5,116,742. Alternatively, Kinase and Phosphatase MRNA can be used to select a catalytic RNA having a specific ribonuclease activity from a pool of RNA molecules. See, e.g., Bartel, D. and Szostak, J. W. (1993) *Science* 261:1411–1418.

Alternatively, Kinase and Phosphatase gene expression can be inhibited by targeting nucleotide sequences complementary to the regulatory region of the Kinase and Phosphatase (e.g., the Kinase and Phosphatase promoter and/or enhancers) to form triple helical structures that prevent transcription of the Kinase and Phosphatase gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the Kinase and Phosphatase nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of Kinase and Phosphatase nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of Kinase and Phosphatase nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of Kinase and Phosphatase can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of Kinase and Phosphatase nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated Kinase and Phosphatase Proteins and Anti-Kinase and Anti-Phosphatase Antibodies One aspect of the invention pertains to isolated Kinase and Phosphatase proteins, and biologically active portions thereof, as well as polypeptide fragments suitable for use as immunogens to raise anti-Kinase and Phosphatase antibodies. In one embodiment, native Kinase and Phosphatase proteins can be isolated from cells or tissue sources by an appropriate purification scheme using standard protein purification techniques. In another embodiment, Kinase and Phosphatase proteins are produced by recombinant DNA techniques. Alternative to recombinant expression, a Kinase and Phosphatase protein or polypeptide can be synthesized chemically using standard peptide synthesis techniques.

An "isolated" or "purified" protein or biologically active portion thereof is substantially free of cellular material or other contaminating proteins from the cell or tissue source from which the Kinase and Phosphatase protein is derived, or substantially free from chemical precursors or other chemicals when chemically synthesized. The language "substantially free of cellular material" includes preparations of Kinase and Phosphatase protein in which the protein is separated from cellular components of the cells from which it is isolated or recombinantly produced. In one embodiment, the language "substantially free of cellular material" includes preparations of Kinase and Phosphatase protein having less than about 30% (by dry weight) of non-Kinase and Phosphatase protein (also referred to herein as a "contaminating protein"), more preferably less than about 20% of non-Kinase and Phosphatase protein, still more preferably less than about 10% of non-Kinase and Phosphatase protein, and most preferably less than about 5% non-Kinase and Phosphatase protein. When the Kinase and Phosphatase protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of Kinase and Phosphatase protein in which the protein is separated from chemical precursors or other chemicals which are involved in the synthesis of the protein. In one embodiment, the language "substantially free of chemical precursors or other chemicals" includes preparations of Kinase and Phosphatase protein having less than about 30% (by dry weight) of chemical precursors or non-Kinase and Phosphatase chemicals, more preferably less than about 20% chemical precursors or non-Kinase and Phosphatase chemicals, still more preferably less than about 10% chemical precursors or non-Kinase and Phosphatase chemicals, and most preferably less than about 5% chemical precursors or non-Kinase and Phosphatase chemicals.

Biologically active portions of a Kinase and Phosphatase protein include peptides comprising amino acid sequences sufficiently homologous to or derived from the amino acid sequence of the Kinase and Phosphatase protein, which include less amino acids than the full length Kinase and Phosphatase proteins, and exhibit at least one activity of a Kinase and Phosphatase protein. Typically, biologically active portions comprise a domain or motif with at least one activity of the Kinase and Phosphatase protein. A biologically active portion of a Kinase and Phosphatase protein can be a polypeptide which is, for example, at least 10, 25, 50, 100 or more amino acids in length.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to Kinase and Phosphatase nucleic acid molecules of the invention. BLAST protein searches can be performed with the XBLAST program, score=50, wordlength=3 to obtain amino acid sequences homologous to Kinase and Phosphatase protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The invention also provides Kinase and Phosphatase chimeric or fusion proteins. As used herein, a Kinase and Phosphatase "chimeric protein" or "fusion protein" comprises a Kinase and Phosphatase polypeptide operatively linked to a non-Kinase and Phosphatase polypeptide. An "Kinase and Phosphatase polypeptide" refers to a polypeptide having an amino acid sequence corresponding to Kinase and Phosphatase, whereas a "non-Kinase and Phosphatase polypeptide" refers to a polypeptide having an amino acid sequence corresponding to a protein which is not substantially homologous to the Kinase and Phosphatase protein, e.g., a protein which is different from the Kinase and Phosphatase protein and which is derived from the same or a different organism. Within a Kinase and Phosphatase fusion protein the Kinase and Phosphatase polypeptide can correspond to all or a portion of a Kinase and Phosphatase protein. In a preferred embodiment, a Kinase and Phosphatase fusion protein comprises at least one biologically active portion of a Kinase and Phosphatase protein. In another preferred embodiment, a Kinase and Phosphatase fusion protein comprises at least two biologically active portions of a Kinase and Phosphatase protein. Within the fusion protein, the term "operatively linked" is intended to indicate that the Kinase and Phosphatase polypeptide and the non-Kinase and Phosphatase polypeptide are fused in-frame to each other. The non-Kinase and Phosphatase polypeptide can be fused to the N-terminus or C-terminus of the Kinase and Phosphatase polypeptide.

For example, in one embodiment, the fusion protein is a GST-Kinase and Phosphatase fusion protein in which the Kinase and Phosphatase sequences are fused to the C-terminus of the GST sequences. Such fusion proteins can facilitate the purification of recombinant Kinase and Phosphatase.

In another embodiment, the fusion protein is a Kinase and Phosphatase protein containing a heterologous signal sequence at its N-terminus. In certain host cells (e.g., mammalian host cells), expression and/or secretion of Kinase and Phosphatase can be increased through use of a heterologous signal sequence.

The Kinase and Phosphatase fusion proteins of the invention can be incorporated into pharmaceutical compositions and administered to a subject in vivo. The Kinase and Phosphatase fusion proteins can be used to affect the bioavailability of a Kinase and Phosphatase substrate. Use of Kinase and Phosphatase fusion proteins may be useful therapeutically for the treatment of cellular growth related disorders, e.g., cancer. Moreover, the Kinase and Phosphatase-fusion proteins of the invention can be used as immunogens to produce anti-Kinase and Phosphatase antibodies in a subject, to purify Kinase and Phosphatase ligands and in screening assays to identify molecules which inhibit the interaction of Kinase and Phosphatase with a Kinase and Phosphatase substrate.

Preferably, a Kinase and Phosphatase chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A Kinase and Phosphatase-encoding nucleic acid can be cloned into such an expression vector such that the fusion moiety is linked in-frame to the Kinase and Phosphatase protein.

The present invention also pertains to variants of the Kinase and Phosphatase proteins which function as either Kinase and Phosphatase agonists (mimetics) or as Kinase and Phosphatase antagonists. Variants of the Kinase and Phosphatase proteins can be generated by mutagenesis, e.g., discrete point mutation or truncation of a Kinase and Phosphatase protein. An agonist of the Kinase and Phosphatase proteins can retain substantially the same, or a subset, of the biological activities of the naturally occurring form of a Kinase and Phosphatase protein. An antagonist of a Kinase and Phosphatase protein can inhibit one or more of the activities of the naturally occurring form of the Kinase and Phosphatase protein by, for example, competitively modulating a cellular activity of a Kinase and Phosphatase protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the Kinase and Phosphatase protein.

In one embodiment, variants of a Kinase and Phosphatase protein which function as either Kinase and Phosphatase agonists (mimetics) or as Kinase and Phosphatase antagonists can be identified by screening combinatorial libraries of mutants, e.g., truncation mutants, of a Kinase and Phosphatase protein for Kinase and Phosphatase protein agonist or antagonist activity. In one embodiment, a variegated library of Kinase and Phosphatase variants is generated by combinatorial mutagenesis at the nucleic acid level and is encoded by a variegated gene library. A variegated library of Kinase and Phosphatase variants can be produced by, for example, enzymatically ligating a mixture of synthetic oligonucleotides into gene sequences such that a degenerate set of potential Kinase and Phosphatase sequences is expressible as individual polypeptides, or alternatively, as a set of larger fusion proteins (e.g., for phage display) containing the set of Kinase and Phosphatase sequences therein. There are a variety of methods which can be used to produce libraries of potential Kinase and Phosphatase variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Kinase and Phosphatase sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a Kinase and Phosphatase protein coding sequence can be used to generate a variegated population of Kinase and Phosphatase fragments for screening and subsequent selection of variants of a Kinase and Phosphatase protein. In one embodiment, a library of coding sequence fragments can be generated by treating a double stranded PCR fragment of a Kinase and Phosphatase coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the Kinase and Phosphatase protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Kinase and Phosphatase proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify Kinase and Phosphatase variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated Kinase and Phosphatase library. For example, a library of expression vectors can be transfected into a cell line which ordinarily synthesizes and secretes Kinase and Phosphatase. The transfected cells are then cultured such that Kinase and Phosphatase and a particular mutant Kinase and Phosphatase are secreted and the effect of expression of the mutant on Kinase and Phosphatase activity in cell supernatants can be detected, e.g., by any of a number of enzymatic assays. Plasmid DNA can then be recovered from the cells which score for inhibition, or alternatively, potentiation of Kinase and Phosphatase activity, and the individual clones further characterized.

An isolated Kinase and Phosphatase protein, or a portion or fragment thereof, can be used as an immunogen to generate antibodies that bind Kinase and Phosphatase using standard techniques for polyclonal and monoclonal antibody preparation. A full-length Kinase and Phosphatase protein can be used or, alternatively, the invention provides antigenic peptide fragments of Kinase and Phosphatase for use as immunogens. The antigenic peptide of Kinase and Phosphatase comprises at least 8 amino acid residues and encompasses an epitope of Kinase and Phosphatase such that an antibody raised against the peptide forms a specific immune complex with Kinase and Phosphatase. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of Kinase and Phosphatase that are located on the surface of the protein, e.g., hydrophilic regions.

A Kinase and Phosphatase immunogen typically is used to prepare antibodies by immunizing a suitable subject, (e.g., rabbit, goat, mouse or other mammal) with the immunogen. An appropriate immunogenic preparation can contain, for example, recombinantly expressed Kinase and Phosphatase protein or a chemically synthesized Kinase and Phosphatase polypeptide. The preparation can further include an adjuvant, such as Freund's complete or incomplete adjuvant, or similar immunostimulatory agent. Immunization of a suitable subject with an immunogenic Kinase and Phosphatase preparation induces a polyclonal anti-Kinase and Phosphatase antibody response.

Accordingly, another aspect of the invention pertains to anti-Kinase and Phosphatase antibodies. The term "antibody" as used herein refers to immunoglobulin molecules and immunologically active portions of immunoglobulin molecules, i.e., molecules that contain an antigen binding site which specifically binds (immunoreacts with) an antigen, such as Kinase and Phosphatase. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind Kinase and Phosphatase. The term "monoclonal antibody" or "monoclonal antibody composition", as used herein, refers to a population of antibody molecules that contain only one species of an antigen binding site capable of immunoreacting with a particular epitope of Kinase and Phosphatase. A monoclonal antibody composition thus typically displays a single binding affinity for a particular Kinase and Phosphatase protein with which it immunoreacts.

Polyclonal anti-Kinase and Phosphatase antibodies can be prepared as described above by immunizing a suitable subject with a Kinase and Phosphatase immunogen. The anti-Kinase and Phosphatase antibody titer in the immunized subject can be monitored over time by standard techniques, such as with an enzyme linked immunosorbent assay (ELISA) using immobilized Kinase and Phosphatase. If desired, the antibody molecules directed against Kinase and Phosphatase can be isolated from the mammal (e.g., from the blood) and further purified by well known techniques, such as protein A chromatography to obtain the IgG fraction. At an appropriate time after immunization, e.g., when the anti-Kinase and Phosphatase antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immuno.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a Kinase and Phosphatase immunogen as described above, and the culture supernatants of the resulting hybridoma cells are screened to identify a hybridoma producing a monoclonal antibody that binds Kinase and Phosphatase.

Any of the many well known protocols used for fusing lymphocytes and immortalized cell lines can be applied for the purpose of generating an anti-Kinase and Phosphatase monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Kinase and Phosphatase, e.g., using a standard ELISA assay.

Alternative to preparing monoclonal antibody-secreting hybridomas, a monoclonal anti-Kinase and Phosphatase antibody can be identified and isolated by screening a recombinant combinatorial immunoglobulin library (e.g., an antibody phage display library) with Kinase and Phosphatase to thereby isolate immunoglobulin library members that bind Kinase and Phosphatase. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-Kinase and Phosphatase antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-Kinase and Phosphatase antibody (e.g., monoclonal antibody) can be used to isolate Kinase and Phosphatase by standard techniques, such as affinity chromatography or immunoprecipitation. An anti-Kinase and Phosphatase antibody can facilitate the purification of natural Kinase and Phosphatase from cells and of recombinantly produced Kinase and Phosphatase expressed in host cells. Moreover, an anti-Kinase and Phosphatase antibody can be used to detect Kinase and Phosphatase protein (e.g., in a cellular lysate or cell supernatant) in order to evaluate the abundance and pattern of expression of the Kinase and Phosphatase protein. Anti-Kinase and Phosphatase antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

III. Recombinant Expression Vectors and Host Cells

Another aspect of the invention pertains to vectors, preferably expression vectors, containing a nucleic acid encoding a Kinase and Phosphatase protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., Kinase and Phosphatase proteins, mutant forms of Kinase and Phosphatase proteins, fusion proteins, and the like).

The recombinant expression vectors of the invention can be designed for expression of Kinase and Phosphatase proteins in prokaryotic or eukaryotic cells. For example, Kinase and Phosphatase proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in Kinase and Phosphatase activity assays, (e.g., direct assays or competitive assays described in detail below), or to generate antibodies specific for Kinase and Phosphatase proteins, for example. In a preferred embodiment, a Kinase and Phosphatase fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the Kinase and Phosphatase expression vector is a yeast expression vector. Examples of vectors for expression in yeast S. cerivisae include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, Kinase and Phosphatase proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufinan et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the a-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to Kinase and Phosphatase MRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a Kinase and Phosphatase protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed.*, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a Kinase and Phosphatase protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a Kinase and Phosphatase protein. Accordingly, the invention further provides methods for producing a Kinase and Phosphatase protein using the host cells of the invention. In one embodiment, the method comprises culturing the host cell of invention (into which a recombinant expression vector encoding a Kinase and Phosphatase protein has been introduced) in a suitable medium such that a Kinase and Phosphatase protein is produced. In another embodiment, the method further comprises isolating a Kinase and Phosphatase protein from the medium or the host cell.

The host cells of the invention can also be used to produce non-human transgenic animals. For example, in one embodiment, a host cell of the invention is a fertilized oocyte or an embryonic stem cell into which Kinase and Phosphatase-coding sequences have been introduced. Such host cells can then be used to create non-human transgenic animals in which exogenous Kinase and Phosphatase sequences have been introduced into their genome or homologous recombinant animals in which endogenous Kinase and Phosphatase sequences have been altered. Such animals are useful for studying the function and/or activity of a Kinase and Phosphatase and for identifying and/or evaluating modulators of Kinase and Phosphatase activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous Kinase and Phosphatase gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a Kinase and Phosphatase-encoding nucleic acid into the male pronuclei of a fertilized oocyte, e.g., by microinjection, retroviral infection, and allowing the oocyte to develop in a pseudopregnant female foster animal. The Kinase and Phosphatase cDNA sequence of SEQ ID NO:1–14 can be introduced as a transgene into the genome of a non-human animal. Alternatively, a nonhuman homologue of a human Kinase and Phosphatase gene, such as a mouse or rat Kinase and Phosphatase gene, can be used as a transgene. Alternatively, a Kinase and Phosphatase gene homologue, such as another Kinase and Phosphatase family member, can be isolated based on hybridization to the Kinase and Phosphatase cDNA sequences of SEQ ID NO:1–14 (described further in subsection I above) and used as a transgene. Intronic sequences and polyadenylation signals can also be included in the transgene to increase the efficiency of expression of the transgene. A tissue-specific regulatory sequence(s) can be operably linked to a Kinase and Phosphatase transgene to direct expression of a Kinase and Phosphatase protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a Kinase and Phosphatase transgene in its genome and/or expression of Kinase and Phosphatase MRNA in tissues or cells of the animals. A transgenic founder animal can then be used to breed additional animals carrying the transgene. Moreover, transgenic animals carrying a transgene encoding a Kinase and Phosphatase protein can further be bred to other transgenic animals carrying other transgenes.

To create a homologous recombinant animal, a vector is prepared which contains at least a portion of a Kinase and Phosphatase gene into which a deletion, addition or substitution has been introduced to thereby alter, e.g., functionally disrupt, the Kinase and Phosphatase gene. The Kinase and Phosphatase gene can be a human gene (e.g., the SEQ ID NO:1–14), but more preferably, is a non-human homologue of a human Kinase and Phosphatase gene (e.g., a cDNA isolated by stringent hybridization with the nucleotide sequence of SEQ ID NO:1–14). For example, a mouse Kinase and Phosphatase gene can be used to construct a homologous recombination vector suitable for altering an endogenous Kinase and Phosphatase gene in the mouse genome. In a preferred embodiment, the vector is designed such that, upon homologous recombination, the endogenous Kinase and Phosphatase gene is functionally disrupted (i.e., no longer encodes a functional protein; also referred to as a "knock out" vector). Alternatively, the vector can be designed such that, upon homologous recombination, the endogenous Kinase and Phosphatase gene is mutated or otherwise altered but still encodes a functional protein (e.g., the upstream regulatory region can be altered to thereby alter the expression of the endogenous Kinase and Phosphatase protein). In the homologous recombination vector, the altered portion of the Kinase and Phosphatase gene is flanked at its 5' and 3' ends by additional nucleic acid sequence of the Kinase and Phosphatase gene to allow for homologous recombination to occur between the exogenous Kinase and Phosphatase gene carried by the vector and an endogenous Kinase and Phosphatase gene in an embryonic stem cell. The additional flanking Kinase and Phosphatase nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced Kinase and Phosphatase gene has homologously recombined with the endogenous Kinase and Phosphatase gene are selected (see, e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The Kinase and Phosphatase nucleic acid molecules, Kinase and Phosphatase proteins, and anti-Kinase and anti-Phosphatase antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a Kinase and Phosphatase protein or anti-Kinase and Phosphatase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g, for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein.

When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express Kinase and Phosphatase protein (e.g., via a recombinant expression vector in a host cell in gene therapy applications), to detect Kinase and Phosphatase MRNA (e.g., in a biological sample) or a genetic alteration in a Kinase and Phosphatase gene, and to modulate Kinase and Phosphatase activity, as described further below. The Kinase and Phosphatase proteins can be used to treat disorders characterized by insufficient or excessive production of a Kinase and Phosphatase substrate or production of Kinase and Phosphatase inhibitors. In addition, the Kinase and Phosphatase proteins can be used to screen for naturally occurring Kinase and Phosphatase substrates, to screen for drugs or compounds which modulate Kinase and Phosphatase activity, as well as to treat disorders characterized by insufficient or excessive production of Kinase and Phosphatase protein or production of Kinase and Phosphatase protein forms which have decreased or aberrant activity compared to Kinase and Phosphatase wild type protein. Moreover, the anti-Kinase and Phosphatase antibodies of the invention can be used to detect and isolate Kinase and Phosphatase proteins, regulate the bioavailability of Kinase and Phosphatase proteins, and modulate Kinase and Phosphatase activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to Kinase and Phosphatase proteins, have a stimulatory or inhibitory effect on, for example, Kinase and Phosphatase expression or Kinase and Phosphatase activity, or have a stimulatory or inhibitory effect on, for example, the expression or activity of a Kinase and Phosphatase substrate.

In one embodiment, the invention provides assays for screening candidate or test compounds which are substrates of a Kinase and Phosphatase protein or polypeptide or biologically active portion thereof. In another embodiment, the invention provides assays for screening candidate or test compounds which bind to or modulate the activity of a Kinase and Phosphatase protein or polypeptide or biologically active portion thereof; e.g., modulate the ability of Kinase and Phosphatase to interact with its cognate ligand. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb. et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990)

Proc. Natl. Acad. Sci. 87:6378–6382); (Felici (1991) *J. MoL. Biol.* 222:301–310); (Ladner supra.).

In another embodiment, an assay is a cell-based assay comprising contacting a cell expressing a Kinase and Phosphatase target molecule (e.g., a Kinase and Phosphatase phosphorylation substrate) with a test compound and determining the ability of the test compound to modulate (e.g. stimulate or inhibit) the activity of the Kinase and Phosphatase target molecule. Determining the ability of the test compound to modulate the activity of a Kinase and Phosphatase target molecule can be accomplished, for example, by determining the ability of the Kinase and Phosphatase protein to bind to or interact with the Kinase and Phosphatase target molecule, or by determining the ability of the Kinase and Phosphatase protein to phosphorylate the Kinase and Phosphatase target molecule.

The ability of the Kinase and Phosphatase protein to phosphorylate a Kinase and Phosphatase target molecule can be determined by, for example, an in vitro kinase assay. Briefly, a Kinase and Phosphatase target molecule, e.g., an immunoprecipitated Kinase and Phosphatase target molecule from a cell line expressing such a molecule, can be incubated with the Kinase and Phosphatase protein and radioactive ATP, e.g., [$\gamma$-$^{32}$P] ATP, in a buffer containing $MgCl_2$ and $MnCl_2$, e.g., 10 mM $MgCl_2$ and 5 mM $MnCl_2$. Following the incubation, the immunoprecipitated Kinase and Phosphatase target molecule can be separated by SDS-polyacrylamide gel electrophoresis under reducing conditions, transferred to a membrane, e.g., a PVDF membrane, and autoradiographed. The appearance of detectable bands on the autoradiograph indicates that the Kinase and Phosphatase substrate has been phosphorylated. Phosphoaminoacid analysis of the phosphorylated substrate can also be performed in order to determine which residues on the Kinase and Phosphatase substrate are phosphorylated. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards.

Determining the ability of the Kinase and Phosphatase protein to bind to or interact with a Kinase and Phosphatase target molecule can be accomplished by determining direct binding. Determining the ability of the Kinase and Phosphatase protein to bind to or interact with a Kinase and Phosphatase target molecule can be accomplished, for example, by coupling the Kinase and Phosphatase protein with a radioisotope or enzymatic label such that binding of the Kinase and Phosphatase protein to a Kinase and Phosphatase target molecule can be determined by detecting the labeled Kinase and Phosphatase protein in a complex. For example, Kinase and Phosphatase molecules, e.g., Kinase and Phosphatase proteins, can be labeled with $^{125}I$, $^{35}S$, $^{14}C$, or $^{3}H$, either directly or indirectly, and the radioisotope detected by direct counting of radioemission or by scintillation counting. Alternatively, Kinase and Phosphatase molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between Kinase and Phosphatase and its target molecule, without the labeling of any of the interactants. For example, a microphysiometer can be used to detect the interaction of Kinase and Phosphatase with its target molecule without the labeling of either Kinase and Phosphatase or the target molecule. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the Kinase and Phosphatase protein to bind to or interact with a Kinase and Phosphatase target molecule can be accomplished by determining the activity of the target molecule. For example, the activity of the target molecule can be determined by detecting induction of a cellular second messenger of the target (e.g., intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response.

In yet another embodiment, an assay of the present invention is a cell-free assay in which a Kinase and Phosphatase protein or biologically active portion thereof is contacted with a test compound and the ability of the test compound to bind to the Kinase and Phosphatase protein or biologically active portion thereof is determined. Binding of the test compound to the Kinase and Phosphatase protein can be determined either directly or indirectly as described above. In a preferred embodiment, the assay includes contacting the Kinase and Phosphatase protein or biologically active portion thereof with a known compound which binds Kinase and Phosphatase to form an assay mixture, contacting the assay mixture with a test compound, and determining the ability of the test compound to interact with a Kinase and Phosphatase protein, wherein determining the ability of the test compound to interact with a Kinase and Phosphatase protein comprises determining the ability of the test compound to preferentially bind to Kinase and Phosphatase or biologically active portion thereof as compared to the known compound.

In another embodiment, the assay is a cell-free assay in which a Kinase and Phosphatase protein or biologically active portion thereof is contacted with a test compound and the ability of the test compound to modulate (e.g., stimulate or inhibit) the activity of the Kinase and Phosphatase protein or biologically active portion thereof is determined. Determining the ability of the test compound to modulate the activity of a Kinase and Phosphatase protein can be accomplished, for example, by determining the ability of the Kinase and Phosphatase protein to bind to a Kinase and Phosphatase target molecule by one of the methods described above for determining direct binding. Determining the ability of the Kinase and Phosphatase protein to bind to a Kinase and Phosphatase target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a Kinase and Phosphatase protein can be accomplished by determining the ability of the Kinase and Phosphatase protein to further modulate the activity of a Kinase and Phosphatase target molecule (e.g., a Kinase and Phosphatase mediated signal transduction pathway component). For example, the activity of the effector molecule on an appropriate target can be determined, or the binding of the effector to an appropriate target can be determined as previously described.

In yet another embodiment, the cell-free assay involves contacting a Kinase and Phosphatase protein or biologically active portion thereof with a known compound which binds the Kinase and Phosphatase protein to form an assay mixture, contacting the assay mixture with a test compound, and determining the ability of the test compound to interact with the Kinase and Phosphatase protein, wherein determining the ability of the test compound to interact with the Kinase and Phosphatase protein comprises determining the ability of the Kinase and Phosphatase protein to preferentially bind to or modulate the activity of a Kinase and Phosphatase target molecule.

The cell-free assays of the present invention are amenable to use of both soluble and/or membrane-bound forms of proteins (e.g., Kinase and Phosphatase proteins or biologically active portions thereof, or receptors to which Kinase and Phosphatase binds). In the case of cell-free assays in which a membrane-bound form a protein is used (e.g., a cell surface Kinase and Phosphatase receptor) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either Kinase and Phosphatase or its target molecule to facilitate separation of complexed from uncomplexed forms of one or both of the proteins, as well as to accommodate automation of the assay. Binding of a test compound to a Kinase and Phosphatase protein, or interaction of a Kinase and Phosphatase protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/ Kinase and Phosphatase fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or Kinase and Phosphatase protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of Kinase and Phosphatase binding or activity determined using standard techniques.

Other techniques for immobilizing proteins on matrices can also be used in the screening assays of the invention. For example, either a Kinase and Phosphatase protein or a Kinase and Phosphatase target molecule can be immobilized utilizing conjugation of biotin and streptavidin. Biotinylated Kinase and Phosphatase protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with Kinase and Phosphatase protein or target molecules but which do not interfere with binding of the Kinase and Phosphatase protein to its target molecule can be derivatized to the wells of the plate, and unbound target or Kinase and Phosphatase protein trapped in the wells by antibody conjugation. Methods for detecting such complexes, in addition to those described above for the GST-immobilized complexes, include immunodetection of complexes using antibodies reactive with the Kinase and Phosphatase protein or target molecule, as well as enzyme-linked assays which rely on detecting an enzymatic activity associated with the Kinase and Phosphatase protein or target molecule.

In another embodiment, modulators of Kinase and Phosphatase expression are identified in a method wherein a cell is contacted with a candidate compound and the expression of Kinase and Phosphatase mRNA or protein in the cell is determined. The level of expression of Kinase and Phosphatase MRNA or protein in the presence of the candidate compound is compared to the level of expression of Kinase and Phosphatase mRNA or protein in the absence of the candidate compound. The candidate compound can then be identified as a modulator of Kinase and Phosphatase expression based on this comparison. For example, when expression of Kinase and Phosphatase mRNA or protein is greater (statistically significantly greater) in the presence of the candidate compound than in its absence, the candidate compound is identified as a stimulator of Kinase and Phosphatase mRNA or protein expression. Alternatively, when expression of Kinase and Phosphatase MRNA or protein is less (statistically significantly less) in the presence of the candidate compound than in its absence, the candidate compound is identified as an inhibitor of Kinase and Phosphatase mRNA or protein expression. The level of Kinase and Phosphatase niRNA or protein expression in the cells can be determined by methods described herein for detecting Kinase and Phosphatase MRNA or protein.

In yet another aspect of the invention, the Kinase and Phosphatase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with Kinase and Phosphatase ("Kinase and Phosphatase-binding proteins" or "Kinase and Phosphatase-bp") and are involved in Kinase and Phosphatase activity. Such Kinase and Phosphatase-binding proteins are also likely to be involved in the propagation of signals by the Kinase and Phosphatase proteins or Kinase and Phosphatase targets as, for example, downstream elements of a Kinase and Phosphatase-mediated signaling pathway. Alternatively, such Kinase and Phosphatase-binding proteins are likely to be Kinase and Phosphatase inhibitors.

The two-hybrid system is based on the modular nature of most transcription factors, which consist of separable DNA-binding and activation domains. Briefly, the assay utilizes two different DNA constructs. In one construct, the gene that codes for a Kinase and Phosphatase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Kinase and Phosphatase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Kinase and Phosphatase protein.

This invention further pertains to novel agents identified by the above-described screening assays. Accordingly, it is within the scope of this invention to further use an agent identified as described herein in an appropriate animal model. For example, an agent identified as described herein (e.g., a Kinase and Phosphatase modulating agent, an antisense Kinase and Phosphatase nucleic acid molecule, a Kinase and Phosphatase-specific antibody, or a Kinase and Phosphatase-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the Kinase and Phosphatase nucleotide sequences, described herein, can be used to map the location of the Kinase and Phosphatase genes on a chromosome. The mapping of the Kinase and Phosphatase sequences to chromosomes is an important first step in correlating these sequences with genes associated with disease.

Briefly, Kinase and Phosphatase genes can be mapped to chromosomes by preparing PCR primers (preferably 15–25 bp in length) from the Kinase and Phosphatase nucleotide sequences. Computer analysis of the Kinase and Phosphatase sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the Kinase and Phosphatase sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the Kinase and Phosphatase nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) *Proc. Natl. Acad Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783–787.

Moreover, differences in the DNA sequences between individuals affected and unaffected with a disease associated with the Kinase and Phosphatase gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The Kinase and Phosphatase sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the Kinase and Phosphatase nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The Kinase and Phosphatase nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1–161, can comfortably provide positive individual identification with a panel of perhaps 10 to 1,000 primers which each yield a noncoding amplified sequence of 100 bases. If predicted coding sequences are used, a more appropriate number of primers for positive individual identification would be 500–2,000.

If a panel of reagents from Kinase and Phosphatase nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial Kinase and Phosphatase Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the Kinase and Phosphatase nucleotide sequences or portions thereof having a length of at least 20 bases, preferably at least 30 bases.

The Kinase and Phosphatase nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such Kinase and Phosphatase probes can be used to identify tissue by species and/or by organ type.

In a similar fashion, these reagents, e.g., Kinase and Phosphatase primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining Kinase and Phosphatase protein and/or nucleic acid expression as well as Kinase and Phosphatase activity, in the context of a biological sample (e.g., blood, serum, cells, tissue) to thereby determine whether an individual is afflicted with a disease or disorder, or is at risk of developing a disorder, associated with aberrant Kinase and Phosphatase expression or activity. The invention also provides for prognostic (or predictive) assays for determining whether an individual is at risk of developing a disorder associated with Kinase and Phosphatase protein, nucleic acid expression or activity. For example, mutations in a Kinase and Phosphatase gene can be assayed in a biological sample. Such assays can be used for prognostic or predictive purpose to thereby phophylactically treat an individual prior to the onset of a disorder characterized by or associated with Kinase and Phosphatase protein, nucleic acid expression or activity.

Another aspect of the invention pertains to monitoring the influence of agents (e.g., drugs, compounds) on the expression or activity of Kinase and Phosphatase in clinical trials.

These and other agents are described in further detail in the following sections.

1. Diagnostic Assays

An exemplary method for detecting the presence or absence of Kinase and Phosphatase protein or nucleic acid in a biological sample involves obtaining a biological sample from a test subject and contacting the biological sample with a compound or an agent capable of detecting Kinase and Phosphatase protein or nucleic acid (e.g., MRNA, genomic DNA) that encodes Kinase and Phosphatase protein such that the presence of Kinase and Phosphatase protein or nucleic acid is detected in the biological sample. A preferred agent for detecting Kinase and Phosphatase mRNA or genomic DNA is a labeled nucleic acid probe capable of hybridizing to Kinase and Phosphatase mRNA or genomic DNA. The nucleic acid probe can be, for example, a human Kinase and Phosphatase nucleic acid, such as the nucleic acid of SEQ ID NO:1–14, or a portion thereof, such as an oligonucleotide of at least 15, 30, 50, 100, 250 or 500 nucleotides in length and sufficient to specifically hybridize under stringent conditions to Kinase and Phosphatase MRNA or genomic DNA. Other suitable probes for use in the diagnostic assays of the invention are described herein.

A preferred agent for detecting Kinase and Phosphatase protein is an antibody capable of binding to Kinase and Phosphatase protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect Kinase and Phosphatase mRNA, protein, or genomic DNA in a biological sample in vitro as well as in vivo. For example, in vitro techniques for detection of Kinase and Phosphatase MRNA include Northern hybridizations and in situ hybridizations. In vitro techniques for detection of Kinase and Phosphatase protein include enzyme linked immunosorbent assays (ELISAs), Western blots, immunoprecipitations and immunofluorescence. In vitro techniques for detection of Kinase and Phosphatase genomic DNA include Southern hybridizations. Furthermore, in vivo techniques for detection of Kinase and Phosphatase protein include introducing into a subject a labeled anti-Kinase and Phosphatase antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Kinase and Phosphatase protein, mRNA, or genomic DNA, such that the presence of Kinase and Phosphatase protein, MRNA or genomic DNA is detected in the biological sample, and comparing the presence of Kinase and Phosphatase protein, MRNA or genomic DNA in the control sample with the presence of Kinase and Phosphatase protein, MRNA or genomic DNA in the test sample.

The invention also encompasses kits for detecting the presence of Kinase and Phosphatase in a biological sample. For example, the kit can comprise a labeled compound or agent capable of detecting Kinase and Phosphatase protein or mRNA in a biological sample; means for determining the amount of Kinase and Phosphatase in the sample; and means for comparing the amount of Kinase and Phosphatase in the sample with a standard. The compound or agent can be packaged in a suitable container. The kit can further comprise instructions for using the kit to detect Kinase and Phosphatase protein or nucleic acid.

2. Prognostic Assays

The diagnostic methods described herein can furthermore be utilized to identify subjects having or at risk of developing a disease or disorder associated with aberrant Kinase and Phosphatase expression or activity. For example, the assays described herein, such as the preceding diagnostic assays or the following assays, can be utilized to identify a subject having or at risk of developing a disorder associated with Kinase and Phosphatase protein, nucleic acid expression or activity. Thus, the present invention provides a method for identifying a disease or disorder associated with aberrant Kinase and Phosphatase expression or activity in which a test sample is obtained from a subject and Kinase and Phosphatase protein or nucleic acid (e.g., mRNA, genomic DNA) is detected, wherein the presence of Kinase and Phosphatase protein or nucleic acid is diagnostic for a subject having or at risk of developing a disease or disorder associated with aberrant Kinase and Phosphatase expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant Kinase and Phosphatase expression or activity. Thus, the present invention provides methods for determining whether a subject can be effectively treated with an agent for a disorder associated with aberrant Kinase and Phosphatase expression or activity in which a test sample is obtained and Kinase and Phosphatase protein or nucleic acid expression or activity is detected (e.g., wherein the abundance of Kinase and Phosphatase protein or nucleic acid expression or activity is diagnostic for a subject that can be administered the agent to treat a disorder associated with aberrant Kinase and Phosphatase expression or activity).

The methods of the invention can also be used to detect genetic alterations in a Kinase and Phosphatase gene, thereby determining if a subject with the altered gene is at risk for a disorder associated with the Kinase and Phosphatase gene. In preferred embodiments, the methods include detecting, in a sample of cells from the subject, the presence or absence of a genetic alteration characterized by at least one of an alteration affecting the integrity of a gene encoding a Kinase and Phosphatase-protein, or the misexpression of the Kinase and Phosphatase gene. For example, such genetic alterations can be detected by ascertaining the existence of at least one of 1) a deletion of one or more nucleotides from a Kinase and Phosphatase gene; 2) an addition of one or more nucleotides to a Kinase and Phosphatase gene; 3) a substitution of one or more nucleotides of a Kinase and Phosphatase gene, 4) a chromosomal rearrangement of a Kinase and Phosphatase gene; 5) an alteration in the level of a messenger RNA transcript of a Kinase and Phosphatase gene, 6) aberrant modification of a Kinase and Phosphatase gene, such as of the methylation pattern of the genomic DNA, 7) the presence of a non-wild type splicing pattern of a messenger RNA transcript of a Kinase and Phosphatase gene, 8) a non-wild type level of a Kinase and Phosphatase-protein, 9) allelic loss of a Kinase and Phosphatase gene, and 10) inappropriate post-translational modification of a Kinase and Phosphatase-protein. As described herein, there are a large number of assay techniques known in the art which can be used for detecting alterations in a Kinase and Phosphatase gene. A preferred biological sample is a tissue or serum sample isolated by conventional means from a subject, e.g., a cardiac tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the Kinase and Phosphatase-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a Kinase and Phosphatase gene under conditions such that hybridization and amplification of the Kinase and Phosphatase-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Kinase and Phosphatase gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in Kinase and Phosphatase can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2:753–759). For example, genetic mutations in Kinase and Phosphatase can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Kinase and Phosphatase gene and detect mutations by comparing the sequence of the sample Kinase and Phosphatase with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the Kinase and Phosphatase gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type Kinase and Phosphatase sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Kinase and Phosphatase cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a Kinase and Phosphatase sequence, e.g., a wild-type Kinase and Phosphatase sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Kinase and Phosphatase genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat Res* 285:125–144; and Hayashi (1992) *Genet Anal Tech Appl* 9:73–79). Single-stranded DNA fragments of sample and control Kinase and Phosphatase nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res*. 17:2437–2448) or at the extreme 3' end of one primer where, under appropriate conditions, mismatch can prevent, or reduce polymerase extension (Prossner et al. (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Kinase and Phosphatase gene.

Furthermore, any cell type or tissue in which Kinase and Phosphatase is expressed may be utilized in the prognostic assays described herein.

3. Monitoring of Effects During Clinical Trials

Monitoring the influence of agents (e.g., drugs or compounds) on the expression or activity of a Kinase and Phosphatase protein can be applied not only in basic drug screening, but also in clinical trials. For example, the effectiveness of an agent determined by a screening assay as described herein to increase Kinase and Phosphatase gene expression, protein levels, or upregulate Kinase and Phosphatase activity, can be monitored in clinical trials of subjects exhibiting decreased Kinase and Phosphatase gene expression, protein levels, or downregulated Kinase and Phosphatase activity. Alternatively, the effectiveness of an agent determined by a screening assay to decrease Kinase and Phosphatase gene expression, protein levels, or downregulate Kinase and Phosphatase activity, can be monitored in clinical trials of subjects exhibiting increased Kinase and Phosphatase gene expression, protein levels, or upregulated Kinase and Phosphatase activity. In such clinical trials, the expression or activity of a Kinase and Phosphatase gene, and preferably, other genes that have been implicated in a disorder can be used as a "read out" or markers of the phenotype of a particular cell.

For example, and not by way of limitation, genes, including Kinase and Phosphatase, that are modulated in cells by treatment with an agent (e.g., compound, drug or small molecule) which modulates Kinase and Phosphatase activity (e.g., identified in a screening assay as described herein) can be identified. Thus, to study the effect of agents on a Kinase and Phosphatase associated disorder, for example, in a clinical trial, cells can be isolated and RNA prepared and analyzed for the levels of expression of Kinase and Phosphatase and other genes implicated in the Kinase and Phosphatase associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of Kinase and Phosphatase or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a Kinase and Phosphatase protein, mRNA, or genomic DNA in the pre-administration sample; (iii) obtaining one or more post-administration samples from the subject; (iv) detecting the level of expression or activity of the Kinase and Phosphatase protein, mRNA, or genomic DNA in the post-administration samples; (v) comparing the level of expression or activity of the Kinase and Phosphatase protein, mRNA, or genomic DNA in the pre-administration sample with the Kinase and Phosphatase protein, mRNA, or genomic DNA in the post administration sample or samples; and (vi) altering the administration of the agent to the subject accordingly. For example, increased administration of the agent may be desirable to increase the expression or activity of Kinase and Phosphatase to higher levels than detected, i.e., to increase the effectiveness of the agent. Alternatively, decreased administration of the agent may be desirable to decrease expression or activity of Kinase and Phosphatase to lower levels than detected, i.e. to decrease the effectiveness of the agent. According to such an embodiment, Kinase and Phosphatase expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant Kinase and Phosphatase expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the Kinase and Phosphatase molecules of the present invention or Kinase and Phosphatase modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant Kinase and Phosphatase expression or activity, by administering to the subject a Kinase and Phosphatase or an agent which modulates Kinase and Phosphatase expression or at least one Kinase and Phosphatase activity. Subjects at risk for a disease which is caused or contributed to by aberrant Kinase and Phosphatase expression or activity can be identified by, for example, any or a combination of diagnostic or prognostic assays as described herein. Administration of a prophylactic agent can occur prior to the manifestation of symptoms characteristic of the Kinase and Phosphatase aberrancy, such that a disease or disorder is prevented or, alternatively, delayed in its progression. Depending on the type of Kinase and Phosphatase aberrancy, for example, a Kinase and Phosphatase, Kinase and Phosphatase agonist or Kinase and Phosphatase antagonist agent can be used for treating the subject. The appropriate agent can be determined based on screening assays described herein.

2. Therapeutic Methods

Another aspect of the invention pertains to methods of modulating Kinase and Phosphatase expression or activity for therapeutic purposes. Accordingly, in an exemplary embodiment, the modulatory method of the invention involves contacting a cell with a Kinase and Phosphatase or agent that modulates one or more of the activities of Kinase and Phosphatase protein activity associated with the cell. An agent that modulates Kinase and Phosphatase protein activity can be an agent as described herein, such as a nucleic acid or a protein, a naturally-occurring target molecule of a Kinase and Phosphatase protein (e.g., a Kinase and Phosphatase phosphorylation substrate), a Kinase and Phosphatase antibody, a Kinase and Phosphatase agonist or antagonist, a peptidomimetic of a Kinase and Phosphatase agonist or antagonist, or other small molecule. In one embodiment, the agent stimulates one or more Kinase and Phosphatase activities. Examples of such stimulatory agents include active Kinase and Phosphatase protein and a nucleic acid molecule encoding Kinase and Phosphatase that has been introduced into the cell. In another embodiment, the agent inhibits one or more Kinase and Phosphatase activites. Examples of such inhibitory agents include antisense Kinase and Phosphatase nucleic acid molecules, anti-Kinase and Phosphatase antibodies, and Kinase and Phosphatase inhibitors. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a Kinase and Phosphatase protein or nucleic acid molecule. In one embodiment, the method involves administering an agent (e.g., an agent identified by a screening assay described herein), or combination of agents that modulates (e.g., upregulates or downregulates) Kinase and Phosphatase expression or activity. In another embodiment, the method involves administering a Kinase and Phosphatase protein or nucleic acid molecule as therapy to compensate for reduced or aberrant Kinase and Phosphatase expression or activity.

Stimulation of Kinase and Phosphatase activity is desirable in situations in which Kinase and Phosphatase is abnormally downregulated and/or in which increased Kinase and Phosphatase activity is likely to have a beneficial effect. For example, stimulation of Kinase and Phosphatase activity is desirable in situations in which a Kinase and Phosphatase is downregulated and/or in which increased Kinase and Phosphatase activity is likely to have a beneficial effect. Likewise, inhibition of Kinase and Phosphatase activity is desirable in situations in which Kinase and Phosphatase is abnormally upregulated and/or in which decreased Kinase and Phosphatase activity is likely to have a beneficial effect.

3. Pharmacogenomics

The Kinase and Phosphatase molecules of the present invention, as well as agents, or modulators which have a stimulatory or inhibitory effect on Kinase and Phosphatase activity (e.g., Kinase and Phosphatase gene expression) as identified by a screening assay described herein can be administered to individuals to treat (prophylactically or therapeutically) disorders (e.g, proliferative disorders such as cancer) associated with aberrant Kinase and Phosphatase activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a Kinase and Phosphatase molecule or Kinase and Phosphatase modulator as well as tailoring the dosage and/or therapeutic regimen of treatment with a Kinase and Phosphatase molecule or Kinase and Phosphatase modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict a drug response. According to this method, if a gene that encodes a drug target is known (e.g., a Kinase and Phosphatase protein or Kinase and Phosphatase receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a Kinase and Phosphatase molecule or Kinase and Phosphatase modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a Kinase and Phosphatase molecule or Kinase and Phosphatase modulator, such as a modulator identified by one of the exemplary screening assays described herein.

This invention is further illustrated by the following examples which should not be construed as limiting. The contents of all references, patents and published patent applications cited throughout this application, as well as the Figures and the Sequence Listing are incorporated herein by reference.

EXAMPLES

Example 1

IDENTIFICATION AND CHARACTERIZATION OF HUMAN KINASE AND PHOSPHATASE cDNAs

In this example, the identification and characterization of the genes encoding human Kinases and Phosphatases is described.

Isolation of the human Kinase and Phosphatase cDNAs

The invention is based, at least in part, on the discovery of human genes encoding members of the Kinase and Phosphatase family. The human Kinase and Phosphatase family members were isolated based on a specific consensus motif or protein domain characteristic of a Kinase or a Phosphatase family of proteins. The search of the nucleic acid sequence database was performed with one or more HMM motifs, a TBLASTN set, or both.

The TBLASTN set included a set of protein sequence probes which correspond to amino acid sequence motifs that are conserved in the protein kinase or the protein phosphatase family of proteins. The protein families used to construct/select the TBLASTN sets used in identifying the Kinase and Phosphatase nucleic acid molecules of the invention are described above.

The HMM motif included a consensus sequence for a protein domain. Such consensus sequences can be found in a database of Hidden Markov Models (HMMs), e.g., the Pfam database, release 2.1, (http://www.sanger.ac.uk/Software/Pfam/HMM_search). A description of the Pfam database can be found in Sonhammer et al. (1997) *Proteins* 28(3)405–420 and a detailed description of HMMs can be found in, for example, Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference. The protein families used to construct/select the HMM motifs used in identifying the Kinase and Phosphatase nucleic acid molecules of the invention are described above.

The sequences of the positive clones were determined and are set forth herein as SEQ ID NOs:1–14.

Example 2

EXPRESSION OF RECOMBINANT KINASE AND PHOSPHATASE PROTEINS IN BACTERIAL CELLS

In this example, Kinases and Phosphatases are expressed as a recombinant glutathione-S-transferase (GST) fusion polypeptide in *E. coli* and the fusion polypeptide is isolated and characterized. Specifically, Kinases and Phosphatases are fused to GST and this fusion polypeptide is expressed in *E. coli*, e.g., strain PEB199. Expression of the GST-Kinase and Phosphatase fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

EXPRESSION OF RECOMBINANT KINASE AND PHOSPHATASE PROTEINS IN COS CELLS

To express the Kinase and/or Phosphatase gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire Kinase and Phosphatase protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the Kinase and Phosphatase DNA sequence is amplified by PCR using two primers. The 5' primer contains the restriction site of interest followed by approximately twenty nucleotides of the Kinase and Phosphatase coding sequence starting from the initiation codon; the 3' end sequence contains complementary sequences to the other restriction site of interest, a translation stop codon, the HA tag or FLAG tag and the last 20 nucleotides of the Kinase and Phosphatase coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the Kinase and/or Phosphatase gene is inserted in the correct orientation. The ligation mixture is transformed into *E. coli* cells (strains HB 101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the Kinase and Phosphatase-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989. The expression of the Kinase and Phosphatase polypeptide is detected by radio labelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the Kinase and/or Phosphatase coding sequence is cloned directly into the polylinker of the pCDNA/Amp vector using the appropriate restriction sites. The resulting plasmid is transfected into COS cells in the manner described above, and the expression of the Kinase and Phosphatase polypeptide is detected by radio labelling and immunoprecipitation using a Kinase and Phosphatase specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound which binds to a Kinase encoded by the nucleotide sequence shown in SEQ ID NOs:1–2, 4–5 or 8–12 comprising:
   a) contacting the Kinase with a test compound under conditions suitable for binding; and
   b) detecting binding of the test compound to the Kinase.

2. The method of claim 1, wherein said detection is by direct binding.

3. The method of claim 2, wherein said direct binding is determined by an immunoprecipitation.

4. The method of claim 2, wherein said direct binding is determined by a yeast two-hybrid assay.

5. A method for identifying a compound which modulates the activity of a Kinase encoded by the nucleotide sequence shown in SEQ ID NOs:1–2, 4–5, or 8–12comprising:
   a) contacting the Kinase or Phosphatase with a test compound; and
   b) determining the effect of the test compound on the activity of the Kinase to thereby identify a compound which modulates the activity of the Kinase.

* * * * *

SEQUENCE LISTING

<160> NUMBER OF SEQ ID NOS: 18

<210> SEQ ID NO 1
<211> LENGTH: 1868
<212> TYPE: DNA
<213> ORGANISM: Homo sapiens
<220> FEATURE:
<223> OTHER INFORMATION: All occurences of n indicate any nucleotide

<400> SEQUENCE: 1

```
gcaattgatc caatatctgc aggtttctaa cacgcaagcc aggacaaaat actcttcaag      60
gacgtgaaca ggaagctgag tgatgtctgg aaggagctct cgctgttact tcaggttgag     120
caacgcatgc ctgtttcacc cataagccaa ggagcgtcct gggcacagga agatcagcag     180
gatgcagacg aagacaggcg agcttttcag atgctaagaa gagataatga aaaaatagaa     240
gcttcactga gacgattaga aatcaacatg aaagaaatca aggaaacttt gaggcagtat     300
ttaccaccaa aatgcatgca ggagatcccg caagagcaaa tcaaggagat caagaaggag     360
cagctttcag gatccccgtg gattctgcta agggaaaatg aagtcagcac actttataaa     420
ggagaatacc acagagctcc agtggccata aaagtattca aaaaactcca ggctggcagc     480
attgcaatag tgaggcagac tttcaataag gagatcaaaa ccatgaagaa attcgaatct     540
cccaacatcc tgcgtatatt tgggatttgc attgatgaaa cagtgactcc gcctcaattc     600
tccattgtca tggagtactg tgaactcggg accctgaggg agctgttgga tagggaaaaa     660
gacctcacac ttggcaagcg catggtccta gtcctggggg cagcccgagg cctataccgg     720
ctacaccatt cagaagcacc tgaactccac ggaaaaatca gaagctcaaa cttcctggta     780
actcaaggct accaagtgaa gcttgcagga tttgagttga ggaaaacaca gacttccatg     840
agtttgggaa ctacgagaga aaagacacga caagagtcaa atctacagca tatctctcac     900
ctcaggaact ggaagatgta ttttatcaat atgatgtaaa gtctgaaata tacagctttg     960
gaatcgtcct ctgggaaatc gccactggag atatcccgtt tcaaggctgt aattctgaga    1020
agatccgcaa gctggtggct gtgaagcggc agcaggagcc actgggtgaa gactgccctt    1080
cagagctgcg ggagatcatt gatgagtgcc cgggcccatg atccctctgt tgcggccctc    1140
tgtggatgaa atcttaaaga aactctccca ccttttctaa gtagtgtatc aaaatctaaa    1200
ccaaggagtc tctggacaag aagctgggag aggcacaaac tggacatcat ctcctcttct    1260
catatccttc ggcattgggt tatctatggg agcaaggagt gggcacgctt ctctgttaca    1320
aatagaaaac gattccagtc atacaggaca catcccactc caaatgatat ttccaaaaac    1380
atacctctga cagtaacttt gatagatggt ttgtcaaatg tatctttctg ggtatccaca    1440
cctcttggca atgaaatttg cagctcctcc cttccataaa tgaagtctct ttccccacca    1500
tttgaatctg ggctggcact gtgacttgat ttgatcaata gaatgtggaa gaagtgactg    1560
tatgccagtt ccaagcctag gtttcaagag gccttataaa tgtctgttgg aaccttaccc    1620
agccatgaac atgttgagtg agcatgctgg agaatgagag accacatgaa gcagaaacat    1680
gctttcctag ctgaagtcat actagcccaa ccaacatggc agctaacaca tgaatgaggc    1740
caatcaagac cagaagaacc actcaagcag atcccagccc aaattgccca ttcacacaat    1800
caggagctaa ataaattact gttgtcttaa aaaaaaaaa aaannnnana nnannnnaan    1860 aannaagg                                                             1868
```

<210> SEQ ID NO 2
<211> LENGTH: 403
<212> TYPE: DNA
<213> ORGANISM: Homo sapiens
<220> FEATURE:
<223> OTHER INFORMATION: All occurences of n indicate any nucleotide

<400> SEQUENCE: 2

```
tactaaaggg aataagcttg cggccgcaat cttttttttt tttttttttt tttttttttt      60
ttttcctaa aanaaaccat ttattgaaaa agaacctttt tcttaaatt tcagtaatca       120
gcctttgca ttacaaacct gcagcttgcc aacaacaaca aaaaggtaa nggtttcaca      180
agtcagngca ctcaacaaac aggagattaa aaacaaggna tgggatgcct gataacacta    240
cancttcttt tgaacctana anggtcaaaa cactncgctg atgtcaccgg ttctcagtcn    300
cgcganacac ggaggaaaca naggcgatgg tccgngtnca gtagtaaggg cacttaacat    360
gcagnttntt taacctcggg gccnccagcc ctccanaggg cct                      403
```

<210> SEQ ID NO 3
<211> LENGTH: 374
<212> TYPE: DNA
<213> ORGANISM: Homo sapiens
<220> FEATURE:
<223> OTHER INFORMATION: All occurences of n indicate any nucleotide

<400> SEQUENCE: 3

```
aatttggccc tcgaggccaa naattcggca cgaggacata agccaccaat ccctgaaaga     60
ttaagccctg aaggaaagga cttcctttct cactgccttg agagtgaccc aaagatgaga   120
tggaccgcca gccagctcct cgaccattcg tttgtcaagg tttgcacaga tgaagaatga   180
agcctagtag aatatggact tggaaaattc tcttaatcac tactgtatgt aatatttaca   240
taaagactgt gctgagaagc aagtataagc ccttttttaac cttccaagna ctgangactg   300
cacaggtgac aagccgtcac ttntcctgct gctcctgttt tgcctgnatg ttggcaaaaa   360
ngccctctgg aagg                                                     374
```

<210> SEQ ID NO 4
<211> LENGTH: 545
<212> TYPE: DNA
<213> ORGANISM: Homo sapiens
<220> FEATURE:
<223> OTHER INFORMATION: All occurences of n indicate any nucleotide

<400> SEQUENCE: 4

```
ggggtgcacc atgctggcca taggggtggg gagagagcca ggcgtcaggg agcctgccgc     60
tttgagcagg ccagacagca ggggatcagg tttcagccca gcttgtattt ttggctgggt   120
gggctggggg ccgaacaggc agcgtcagct gcccatcccc agcacacacc acactcacac   180
tacctttacc cagatagggc accatccact gcccccaccc cccagccccc ctgcaggcag   240
aaaggaatca ggtgctcctg ggctattgaa tnactttagg ntttnttgga ctgtggctaa   300
ttttttggaa ggncttcttg atccgcaacg cnggtgagnn nggcagaggg gtttggntac   360
cagnactccc gcatnatntn angctagngc ctgagangac ccgggtctgc naccaacccg   420
gtttagggat gggggggggt ctgttgantc cncacacncc accttntttta tgtcctcaaa   480
ggctggggtc nttgggccac cacattnnta caaagggggtn ggtctataan tcctcccncg   540
aatgc                                                                545
```

<210> SEQ ID NO 5

<211> LENGTH: 361
<212> TYPE: DNA
<213> ORGANISM: Homo sapiens
<220> FEATURE:
<223> OTHER INFORMATION: All occurences of n indicate any nucleotide

<400> SEQUENCE: 5

```
cgcgtccgag cagtgccctc naggatcctg aagcagtaca gccaccccaa catcgtgcgt      60
ctcattggtg tctgcaccca gaagcagccc atctacatcg tcatggagct tgtgcagggg     120
ggcgacttcc tgaccttcct ccgcacggag ggggcccgcc tgcgggtgaa gactctgctg     180
cagatggtgg gggatgcagc tgctggcatg gagtacctgg agagcaagtg ctgcatccac     240
cgggacctgg ctgctcggaa ctgcctggtg acagagaaga atgtcctgaa gaatcagtga     300
cttttgggga tgtcccgagag aagcccgat tgggggtcta tgcagcctca ggggcctca     360
g                                                                     361
```

<210> SEQ ID NO 6
<211> LENGTH: 467
<212> TYPE: DNA
<213> ORGANISM: Homo sapiens

<400> SEQUENCE: 6

```
gatggtttat tccaaagctg tggacggtga acattaagac gaaagaggtg actcgcgtgg      60
aacctgaaac acggacgcct ttcttccaag aagggctgtg gcgatcaggc cactcaaggc     120
agccagcccc tcagcagggc acgatggcta atgctgcctg gaccgcagga cttttgttc     180
gatttcaaga caccagactc cctctccttc tcagggtcga agacttctgg atgaggaggc     240
tgtgacagat attgcagatc ttcaccgcgt cggggtacgt ctcccggatg tattgctcca     300
tctccaggat ggcccggccg tgcagggtga actccccttc cttctcaatc agccacttgt     360
tttgaacaaa cttctgcagc acctgctccg cttccttctt cctcatcttc ttgccttta     420
gttgatcaac caggttcaat atgtttgtgg aagacgcaaa gccggtt                   467
```

<210> SEQ ID NO 7
<211> LENGTH: 1260
<212> TYPE: DNA
<213> ORGANISM: Homo sapiens
<220> FEATURE:
<223> OTHER INFORMATION: All occurences of n indicate any nucleotide

<400> SEQUENCE: 7

```
aagggaataa gcttgcggcc gcatctnntt tnnntnnnnn tttnttttt ttttttttt       60
ttgcagcaac ttcccaggat ggtttattcc aaagctgtgg acggtgaaca ttaagacgaa     120
agaggtgact cgcgtggaac ctgaaacacg gacgcctttc ttccaagaag ggctgtggcg     180
atcaggccac tcaaggcagc cagcccctca gcagggcacg atggctaatg ctgcctggac     240
cgcagggact ttttgttcga tttcaagaca ccagactccc tctccttctc agggtcgaag     300
acttttggga tctcgtgggg ccagtagtcg ttgcagtggg ggcagcgcgg ttcagcattc     360
gactggaagt acttggccac gcagggtaag tgcatcctga tcccacaggt ttcgcagctt     420
tgaccctgga tgaggaggct gtgacagata ttgcagatct tcaccgcgtc ggggtacgtc     480
tcccggatgt attgctccat ctccaggatg gcccggccgt gcagggtgaa ctccccttcc     540
ttctcaatca gccacttgtt ttgaacaaac ttctgcagca cctgctccgc ttccttcttc     600
ctcatcttct tgcctttaag ttgatcaacc aggttcaata tgtttgtgga agacgcaaag     660
ccggtttctg agtcaataat cagttccaga gcctttctaa acaaatccag ttcattctct     720
```

```
gcaaaatccg tagccatttt ggaaattgaa gttgtagcaa gattcaccaa cgcataaatg      780
ggtctcccat catcttccgt gactcctctc tttatctcaa tatacaagga ctccaagaca      840
ctgttaatgt tgttgatgaa gtcctccaac ttatctacgg tggcattgcg gtcatggacc      900
ttgtagcagt gcgtctgcaa gcgcttcacg tcccattcct ctagcacgcc atgggtcatc      960
agcaactgga ggaagcgccg gtggacatca gtcatgacgc ccattctcct tgtgctgccc     1020
tgcatgtggg aacgaacagg gagcccaagc gcatcccagg ccgcgctagc ggatacggcc     1080
tcgaggctgt aacataagcg gctgcggact tgtacaaagt aagaaactcc gtacacaaaa     1140
cagaggggag cacggagggc ggcgggacaa gagggtggt cggcaaaggc tgtattttcc      1200
atagatgtaa tcacagtttg aatcgaaata caactactcc ttcctcacca ctcagcccaa     1260
```

<210> SEQ ID NO 8
<211> LENGTH: 473
<212> TYPE: DNA
<213> ORGANISM: Homo sapiens
<220> FEATURE:
<223> OTHER INFORMATION: All occurences of n indicate any nucleotide

<400> SEQUENCE: 8

```
cgcgtccgcg cggtgtatgc tgagccgctg ccgcagcggg ctgctccacg tcctgggcct       60
tagcttcctg ctgcagaccc gccggccgat tctcctctgc tctccacgtc tcatgaagcc      120
gctggtcgtg ttcgtcctcg gcggcccecgg cgccggcaag gggacccagt gcgcccgcat     180
cgtcgaggaa atggatcaga caatggctgc caatgctcag aagaataaat tcttgattga     240
tgggtttcca agaaatcaag acaaccttca aggatggaac aagaccatgg atgggaaggc     300
agatgtatct ttcgttctct tttttgactg taataatgag atttgtattg aacgatgtct     360 tgagaggga aagagtagtg gtgnnanttg gatgacaaca nagagagctt ggaaaagaga     420
attcagncct accttcagnc aacaaagcca atttattgac ttatattgaa gaa            473
```

<210> SEQ ID NO 9
<211> LENGTH: 3001
<212> TYPE: DNA
<213> ORGANISM: Homo sapiens

<400> SEQUENCE: 9

```
cggcgccggc tcagcccgcc cctttctccc gccgcctccc cgccccgccc cgcgccgcgc       60
cggccgctgt cagctccctc agcgtccggc cgaggcgcgg tgtatgctga gccgctgccg     120
cagccggctg ctccacgtcc tgggccttag cttcctgctg cagacccgcc ggccgattct     180
cctctgctct ccacgtctca tgaagccgct ggtcgtgttc gtcctcggcg gccccggcgc     240
cggcaagggg acccagtgcg cccgcatcgt cgagaaatat ggctacacac acctttctgc     300
aggagagctg cttcgtgatg aaaggaagaa cccagattca cagtatggtg aacttattga     360
aaagtacatt aaagaaggaa agattgtacc agttgagata accatcagtt tattaaagag     420
ggaaatggat cagacaatgg ctgccaatgc tcagaagaat aaattcttga ttgatgggtt     480
tccaagaaat caagacaacc ttcaaggatg gaacaagacc atggatggga aggcagatgt     540
atctttcgtt ctctttttg actgtaataa tgagatttgt attgaacgat gtctgagag      600 gggaaagagt agtggtagga gtgatgacaa cagagagagc ttggaaaaga gaattcagac     660
ctaccttcag tcaacaaagc caattattga cttatatgaa gaaatgggga agtcaagaa      720 aatagatgct tctaaatctg ttgatgaagt ttttgatgaa gttgtgcaga ttttgacaa      780
```

-continued

```
ggaaggctaa ttctaaacct gaaagcatcc ttgaaatcat gcttgaatat tgctttgata    840
gctgctatca tgaccccttt ttaaggcaat tctaatcttt cataactaca tctcaattag    900
tggctggaaa gtacatggta aaacaaagta aattttttta tgttcttttt tttggtcaca    960
ggagtagaca gtgaattcag gtttaacttc accttagtta tggtgctcac caaacgaagg   1020
gtatcagcta tttttttttta aattcaaaaa gaatatccct tttatagttt gtgccttctg   1080
tgagcaaaac ttttagtac gcgtatatat ccctctagta atcacaacat tttaggattt    1140
agggatacct gcttcctctt tttcttgcaa gttttaaatt tccaaccctta agtgaatttg   1200
tggaccaaat ttcaaaggaa cttttgtgt agtcagttct tgcacaatgt gtttggtaaa    1260
caaactcaaa atggattctt aggagcattt tagtgtttat taaataactg accatttgct   1320
gtagaaagat gagaaaactt aagctttgtt ttactacaac ttgtacaaag ttgtatgaca   1380
gggcatattc tttgcttcca agatttgggt tgggggcact aggggttcag agcctggcag   1440
aattgtcagc tttagtctga cataatctaa gggtatgggg caaggatcac atctaatgct   1500
tgtgttcctt atactctatt atatagtgtt attcatgatt cagctgatct taacaaaatt   1560
cgtagcagtg gaaccttgaa atgcatgtgg ctagatttat gctaaaatga ttctcagtta   1620
gcattttagt aacacttcaa aggtttttttt ttgtttgttt tctagactta ataaaagctt   1680
aggattaatt agaagaagca atctagttaa atttcccatt tgtatttttat tttcttgaat   1740
acttttttca tagttatttg tttaaaaaga tttaaaaatc attgcacttt ggtcagaaaa   1800
ataataaata tatcttataa atgtttgatt cccttccttg ctattttttat tcagtagatt   1860
tttgtttggc atcatgttga agcaccgaaa gataaatgat ttttaaaagg ctatagagtc   1920
caaaggaata ttcttttaca ccaattcttc ctttaaaaat ctctgaggaa tttgttttcg   1980
ccttactttt ttttcttctg tcacaatgct aagtggtatc cgaggttctt aatatgagat   2040
ttaaaatctt aaaatgtttc ttattttcag cacttacatc atttggtaca cagggtcaaa   2100
tagggcaaat aattttgtct ttgtataata gatttgatat ttaaagtcac tggaaatagg   2160
acaagttaat ggatgttttt atattttaat agaatcattt atttctatgt gttatgaaat   2220
tcacttaatg ataaattttt caacatactt gccattagaa acaaagtat tgctaagtac    2280
tataacatat tggccactaa aattcatatt gagattatct tggtttcttg gaagagatag   2340
gaatgagttc ttatctagtg ttgcaggcca gcaaatacag aggtggttta atcaaacagc   2400
tctagtatga agcaagagta aagactaagg tttcgagagc attcctactc acataagtga   2460
agaaatctgt cagataggaa tctaaatatt tatagtgaga ttgtgaaagc aaccttaaag   2520
ttttgaagaa gactgatgag actaggtgct ttgcttcctt tcatcaggta tcttctgtg    2580
gcatttgaga acagaaacca agaaacatgg taattactaa attatgaggc tttgctttt    2640
gtttgctttt aagtagaaaa acatgttggc aacattgagt tttggagttg attgagataa   2700
tatgacttaa ctagttttgt cattccattt gttaaagata cagtcaccaa gaatgttttg   2760
agttttttga aagaccccaa tttaagccct gcttattttt aaattattc cattcagtga    2820
tgttggatgt atatcagtta tttagtaaat aatctcaata aattttgtgc tgtggccttt   2880
gctaaaaaaa aaaaaaaata ttggtgactg tatctttaac aaatggaatg acaaaactag   2940
ttaagtcata ttatctcaat caactccaaa actcaatgtt gccaacatgt ttttctactt   3000
a                                                                  3001
```

<210> SEQ ID NO 10
<211> LENGTH: 526

<212> TYPE: DNA
<213> ORGANISM: Homo sapiens
<220> FEATURE:
<223> OTHER INFORMATION: All occurences of n indicate any nucleotide

<400> SEQUENCE: 10

| | | |
|---|---|---|
| ncncgtccgg tgacctgaag tcggacaaca ttctggtgtg gtcccttgac gtcaaggagc | 60 |
| acatcaacat caagctatct gactacggga tttcgaggca gtcattccat gagggcgccc | 120 |
| taggcgtgga gggcactcct ggctaccagg ccccagagat caggcctcgc attgtatatg | 180 |
| atgagaaggt agatatgttc tcctatggaa tggtgctcta cgagttgctg tcaggacagc | 240 |
| gccctgcact gggccaccac cagctccaga ttgccaagaa gctgtccaag gcatccgcc | 300 |
| cggttctggg gcagccggag gaagtgcagt tccggcgact gcaggcgctc atgatggagt | 360 |
| gctgggacac taagccagag aagcgaccac tggccctgtc ggtggtgaag ccagatgaag | 420 |
| gacccgactt tgccaccctt catgtatgaa ctgtgctgtg ggaagcagac agccttcttc | 480 |
| ttcatnccag ggccaggagt acactgtggg tgttttggga tggaaa | 526 |

<210> SEQ ID NO 11
<211> LENGTH: 683
<212> TYPE: DNA
<213> ORGANISM: Homo sapiens
<220> FEATURE:
<223> OTHER INFORMATION: All occurences of n indicate any nucleotide

<400> SEQUENCE: 11

| | | |
|---|---|---|
| ttttttttttt caataacaaa ggtccagtat tacccacaac aaagacaaat attttcaaca | 60 |
| tagaacaata agagatattg atacccctatg agcttgttac atctctgtca ttttacacat | 120 |
| tgagatcaaa atccaaacac caggaggccc tctggtaaaa gagtgctggc tgcctaccca | 180 |
| acattctccc ctaatgtctt agtgtcagaa ccccttttgt attagggata gtcacgtacc | 240 |
| cagcaaataa gccacatctc ccagcctcca ttccaggtag gggtgggtgg ttagtgagat | 300 |
| ggaagcagaa gtcattgggt ggagcttttg ggaaagctct ttaaaagcgc cctttgctct | 360 |
| tctcccttt cctccatttt cccttcccta aacacaaaat aggcagctag agctccagta | 420 |
| accatcttgt agcaaaccta acattggaag ccatttgtca aggttggcag ggcagagata | 480 |
| cagcctctga gtatctgatg acctgtcctg ccagtcctgg actccgaaac attattttc | 540 |
| ttttatgtgc tggaaaaaat aaacctgctt ctcgttgaag ccattgntag tttgagtcgc | 600 |
| tcttcctagc agctgaaggt aattccttac taataccagc tggcctcagt agtttcacag | 660 |
| gtccttccgg acgcggggtc gac | 683 |

<210> SEQ ID NO 12
<211> LENGTH: 1448
<212> TYPE: DNA
<213> ORGANISM: Homo sapiens
<220> FEATURE:
<223> OTHER INFORMATION: All occurences of n indicate any nucleotide

<400> SEQUENCE: 12

| | | |
|---|---|---|
| tcagatccca atctccccc aagtatctcg tcacaaatca cactatcgta atcgagaaca | 60 |
| ctttgctact atacggacag catcactggt tacgaggcaa atgcaagaac atgagcagga | 120 |
| ctctgagctt agagaacaaa tgtctggcta agcggaat gaggcgacaa catcaaaagc | 180 |
| aactgatgnc tctggaaaac aagctaaagg ctgagtgga tgaacatcgc ctcagattag | 240 |
| acaaagatct tgaaactcag cgtaacaatt ttgctgcaga aatggagaaa cttatcaaga | 300 |

-continued

| | |
|---|---|
| aacaccaggc tgctatggag aaagaggcta aagtgatgtc caatgaagag aaaaaatttc | 360 |
| agcaacatat tcaggcccaa cagaagaaag aactgaatag ttttctcgag tcccagaaaa | 420 |
| gagagtataa acttcgaaaa gagcagctta agaggagct aaatgaaaac cagagtaccc | 480 |
| ccaaaaaaga aaaacaggag tggctttcaa agcagaagga gaatatacag catttccaag | 540 |
| cagaagaaga agctaccttc ttcgacgtca aagacaatac ctagagctgg aatgcccgtc | 600 |
| gcttcaagag aagaatgtta cttgggcgtc ataacttaga gcaggacctt gtcagggagg | 660 |
| agttaaacaa aagacagact cagaaggact tagagcatgc catgctactc cgacagcatg | 720 |
| aatctatgca agaactggag ttccgccacc tcaacacaat tcagaagatg cgctgtgagt | 780 |
| tgatcagatt acagcatcaa actgagctca ctaaccagct ggaatataat aagcgaagag | 840 |
| aacgagaact aagacgaaag catgtcatgg aagttcgaca acagcctaag agtttgaagt | 900 |
| ctaaagaact ccaaataaaa aagcagtttc aggatacctg caaatccaa accagacagt | 960 |
| acaaagcatt aagaaatcac ctgctggaga ctacaccaaa gagtgagcac aaagctgttc | 1020 |
| tgaaacggct caaggaggaa cagacccgga aattagctat cttggctgag cagtatgatc | 1080 |
| acagcattaa tgaaatgctc tccacacaaa ccgtgggttt gctttttttg gggcaaaaca | 1140 |
| aatttagtgc ccctttctt ccccacctg aacgaaatca cagcaattaa agtactagtt | 1200 |
| ggaaatgata gctctcccga gcttatcaaa aaaaaaaaa aaaaaaaaa aaaaaaaac | 1260 |
| aacatggtga aaccctgtct ctgctgaaag tacaaaaatt agttgggtgt ggcggcacat | 1320 |
| gcctgtggtc ccagctactc gggggctga agcaggagaa tcccttgaac ccaggaggca | 1380 |
| gaggttgcag tgagtcaaga acacaccaca gcactccagc ccgggtgaca gagcaagacc | 1440 |
| ctgtctca | 1448 |

<210> SEQ ID NO 13
<211> LENGTH: 521
<212> TYPE: DNA
<213> ORGANISM: Homo sapiens

<400> SEQUENCE: 13

| | |
|---|---|
| tctcggcccg gctgcgccag agtccgcgcg atggagcccc ggccgcggcg gcggcgcagg | 60 |
| agtcgccccc tggtcgccgc cttcctgcga gacccgggct cgggccgcgt gtacaggcgc | 120 |
| gggaagctga tcggcaaggg cgccttcagc cgctgctaca agctgacaga catgtccacc | 180 |
| agcgccgtgt tcgccctcaa ggtggtgccg tgtggcgggg ctgggccgg gtggcttcgc | 240 |
| ccgcagggaa aggtggagcg tgagattgcc ctgcatagcc gcctgcgacc ccgcaacatc | 300 |
| gtggctttcc acggacactt tgctgaccgc gaccacgtgt acatggtgct ggagtactgc | 360 |
| agccgccagt cttttggccca cgtgctgagg gcgcggcaga tcctgacgga gccagaagtg | 420 |
| cgcgactacc tgcggggcct ggtcagcggc ctgcgctacc tgcaccagcg gtgcatcctg | 480 |
| caccgcgacc tgaagctcag taacttcttc cttaacaaga a | 521 |

<210> SEQ ID NO 14
<211> LENGTH: 481
<212> TYPE: DNA
<213> ORGANISM: Homo sapiens

<400> SEQUENCE: 14

| | |
|---|---|
| ggctgatttt ggtcttgccc gggccaagtc cattcccagc cagacatact cttcagaagt | 60 |
| cgtgaccctc tggtaccggc ccctgatgc tttgctggga gccactgaat attcctctga | 120 |
| gctggacata tggggtgcag gctgcatctt tattgaaatg ttccagggtc aacctttgtt | 180 |

```
tcctggggtt tccaacatcc ttgaacagct ggagaaaatc tgggaggtgc tgggagtccc    240
tacagaggat acttggccgg gagtctccaa gctacctaac tacaatccag aatggttccc    300
actgcctacg cctcgaagcc ttcatgttgt ctggaacagg ctgggcaggg ttcctgaagc    360
tgaagacctg gcctcccaga tgctaaaagg ctttcccaga gaccgcgtct ccgcccagga    420
agcacttgtt catgattatt tcagcgccct gccatctcag ctgtaccagc ttcctgatga    480
g                                                                    481
```

<210> SEQ ID NO 15
<211> LENGTH: 86
<212> TYPE: PRT
<213> ORGANISM: Homo sapiens
<220> FEATURE:
<223> OTHER INFORMATION: ANY 13 OF THE Xaa's AT POSITIONS 42-59 MAY BE
      ABSENT-INTENDED TO EQUAL A RANGE OF 5-18 AMINO ACIDS

<400> SEQUENCE: 15

```
Leu Ile Val Gly Pro Gly Pro Phe Tyr Trp Met Gly Ser Thr Asn His
 1               5                  10                  15

Ser Gly Ala Pro Trp Leu Ile Val Cys Ala Thr Pro Asp Xaa Gly Ser
            20                  25                  30

Thr Ala Cys Leu Ile Val Met Phe Tyr Xaa Xaa Xaa Xaa Xaa Xaa
        35                  40                  45

Xaa Xaa Xaa Xaa Xaa Xaa Xaa Xaa Xaa Xaa Xaa Leu Ile Val Met Phe
    50                  55                  60

Tyr Trp Cys Ser Thr Ala Arg Ala Ile Val Pro Leu Ile Val Met Phe
65                  70                  75                  80

Ala Gly Cys Lys Arg Lys
                85
```

<210> SEQ ID NO 16
<211> LENGTH: 46
<212> TYPE: PRT
<213> ORGANISM: Homo sapiens
<220> FEATURE:
<223> OTHER INFORMATION: AT POSITIONS 8,11,20,21 Xaa = ANY AMINO ACID

<400> SEQUENCE: 16

```
Leu Ile Val Met Phe Tyr Cys Xaa His Tyr Xaa Asp Leu Ile Val Met
 1               5                  10                  15

Phe Tyr Lys Xaa Xaa Asn Leu Ile Val Met Phe Tyr Cys Thr Leu Ile
            20                  25                  30

Val Met Phe Tyr Cys Thr Leu Ile Val Met Phe Tyr Cys Thr
        35                  40                  45
```

<210> SEQ ID NO 17
<211> LENGTH: 47
<212> TYPE: PRT
<213> ORGANISM: Homo sapiens
<220> FEATURE:
<223> OTHER INFORMATION: AT POSITIONS 8,11,24, AND 25 Xaa = ANY AMINO
      ACID

<400> SEQUENCE: 17

```
Leu Ile Val Met Phe Tyr Cys Xaa His Tyr Xaa Asp Leu Ile Val Met
 1               5                  10                  15

Phe Tyr Arg Ser Thr Ala Cys Xaa Xaa Asn Leu Ile Val Met Phe Tyr
            20                  25                  30

Cys Leu Ile Val Met Phe Tyr Cys Leu Ile Val Met Phe Tyr Cys
```

```
<210> SEQ ID NO 18
<211> LENGTH: 33
<212> TYPE: PRT
<213> ORGANISM: Homo sapiens
<220> FEATURE:
<223> OTHER INFORMATION: AT POSITIONS 29,30, AND 31 Xaa = ANY AMINO ACID

<400> SEQUENCE: 18

Leu Ile Val Met Phe Tyr Trp Leu Ile Val Met Phe Tyr Trp Leu Ile
 1               5                  10                  15
Val Met Phe Tyr Trp Asp Gly Phe Tyr Ile Pro Arg Xaa Xaa Xaa Asn
            20                  25                  30
Gln
```